US006861234B1

(12) United States Patent
Simard et al.

(10) Patent No.: US 6,861,234 B1
(45) Date of Patent: Mar. 1, 2005

(54) METHOD OF EPITOPE DISCOVERY

(75) Inventors: John J. L. Simard, Northridge, CA (US); David C. Diamond, Duarte, CA (US)

(73) Assignee: MannKind Corporation, Valencia, CA (US)

( * ) Notice: Subject to any disclaimer, the term of this patent is extended or adjusted under 35 U.S.C. 154(b) by 0 days.

(21) Appl. No.: 09/561,074

(22) Filed: Apr. 28, 2000

(51) Int. Cl.$^7$ .............................................. C12Q 1/02
(52) U.S. Cl. .............................. 435/29; 435/4; 435/23; 435/7.8; 436/86; 436/89; 702/19
(58) Field of Search ........................ 702/19; 435/17.24, 435/7.8, 23; 436/86, 89

(56) References Cited

U.S. PATENT DOCUMENTS

| | | |
|---|---|---|
| 4,439,199 A | 3/1984 | Amkraut et al. |
| 4,683,199 A | 7/1987 | Palladino |
| 4,937,190 A | 6/1990 | Palmenberg et al. |
| 5,093,242 A | 3/1992 | Bachmair et al. |
| 5,132,213 A | 7/1992 | Bachmair et al. |
| 5,149,783 A | 9/1992 | Sommergruber et al. |
| 5,168,062 A | 12/1992 | Stinski |
| 5,258,294 A | 11/1993 | Boyle et al. |
| 5,385,839 A | 1/1995 | Stinski |
| 5,478,556 A | 12/1995 | Elliott et al. |
| 5,496,360 A | 3/1996 | Hoffman et al. |
| 5,496,721 A | 3/1996 | Bachmair et al. |
| 5,580,859 A | 12/1996 | Felgner et al. |
| 5,589,466 A | 12/1996 | Felgner et al. |
| 5,646,017 A | 7/1997 | Bachmair et al. |
| 5,679,647 A | 10/1997 | Carson et al. |
| 5,698,396 A | 12/1997 | Pfreundschuh |
| 5,733,548 A | 3/1998 | Restifo et al. |
| 5,744,316 A | 4/1998 | Lethe et al. |
| 5,747,269 A | 5/1998 | Rammensee et al. |
| 5,759,551 A | 6/1998 | Ladd et al. |
| 5,844,075 A | 12/1998 | Kawakami et al. |
| 5,846,540 A | 12/1998 | Restifo et al. |
| 5,847,097 A | 12/1998 | Bachmair et al. |
| 5,856,187 A | 1/1999 | Restifo et al. |
| 5,869,453 A | 2/1999 | Moss et al. |
| 5,880,103 A | 3/1999 | Urban et al. |
| 5,912,167 A | 6/1999 | Palmenberg et al. |
| 5,925,565 A | 7/1999 | Berlioz et al. |
| 5,962,428 A | 10/1999 | Carrano et al. |
| 5,989,565 A | 11/1999 | Storkus et al. |
| 5,993,828 A | 11/1999 | Morton |
| 5,994,523 A | 11/1999 | Kawakami et al. |
| 6,037,135 A | 3/2000 | Kubo et al. |
| 6,060,273 A | 5/2000 | Dirks et al. |
| 6,287,569 B1 | 9/2001 | Kipps et al. |
| 2003/0186355 A1 | 10/2003 | Ossendorp et al. |

FOREIGN PATENT DOCUMENTS

| | | |
|---|---|---|
| CA | 2147863 | 5/1994 |
| EP | 93/03175 | 4/1995 |
| EP | 1 118 860 A1 | 7/2001 |
| IE | 74899 | 8/1997 |
| WO | 92/21033 | 11/1992 |
| WO | WO96/01429 | 1/1996 |
| WO | WO 96/40209 | 12/1996 |
| WO | WO97/34613 * | 9/1997 |
| WO | WO 97/41440 A1 | 11/1997 |
| WO | WO 97/41440 | 11/1997 |
| WO | WO 98/13489 | 4/1998 |
| WO | WO 98/14464 | 4/1998 |
| WO | WO 99/24596 A1 | 5/1999 |
| WO | WO 01/090197 A1 | 11/2001 |

OTHER PUBLICATIONS

US 6,008,200, 12/1999, Krieg (withdrawn)
Shimbara et al., Genes to Cells vol. 2, pp. 785–800, 1997.*
Groettrup et al. JBC vol. 270: pp. 23808–23815, 1995.*
Ausubel, Frederick M. et al., *Short Protocols in Molecular Biology*, Third Edition, Unit 11.2, pp. 11–5—11–16 (1997).
Carulli, John P. et al., "High Throughput Analysis of Differential Gene Expression", *Journal of Cellular Biochemistry Supplements*, vol. 30/31:286–296 (1998).
Falk, Kirsten et al., "Allele–specific motifs revealed by sequencing of self–peptides eluted from MHC molecules", Nature, vol. 351, pp. 290–295 (May 23, 1991).
Kawakami, Yutaka, et al. "Cloning of the gene coding for a shared human melanoma antigen recognized by autologous T cells infiltrating into tumor", Proc. Natl. Acad. Sci. USA, vol. 91, pp. 3515–3519 (Apr. 1994).
NCBI Blast Accession No. NO_005502, 2 pages.
Türeci, Özlem, et al. "*Identification of a meiosis–specific protein as a member of the class of cancer / testis antigens*", Proc. Natl. Acad. Sci. USA, vol. 95, pp. 5211–5216 (Apr. 1998).
Williams, Kevin P., et al., "*Isolation of a Membrane–Associated Cathespin D–like Enzyme from a Model Antigen Presenting Cell, A20, and its ability to Generate Antigenic Fragments from a Protein Antigen in a Cell–Free System*", vol. 305, No. 2pp. 298–306 (Sep. 1993).
International Search Report re International Application No. PCT/US02/36098 Date of Mailing of International Search Report: Jan. 15, 2004.
Van Den Eynde, et al. "*Differential processing of class–I–restricted epitopes by the standard proteasome and the immunoproteasome,*" Current Opinion in Immunology, vol. 13, pp. 147–153 (2001).
International Search Report re International Application No. PCT/US03/26231 Date of Mailing of International Search Report: Dec. 2, 2003.

(List continued on next page.)

*Primary Examiner*—Patrick J. Nolan
(74) *Attorney, Agent, or Firm*—Knobbe, Martens, Olson & Bear LLP

(57) ABSTRACT

A method of epitope discovery comprising the step of selecting an epitope from a population of peptide fragments of an antigen associated with a target cell, wherein the fragments have a known or predicted affinity for a major histocompatibility complex class I receptor peptide binding cleft, wherein the epitope selected corresponds to a proteasome cleavage product of the target cell.

19 Claims, 3 Drawing Sheets

OTHER PUBLICATIONS

International Search Report re International Application No. PCT/US02/35582 Date of Mailing of International Search Report: Nov. 14, 2003.

Elke Jäger et al., "Identification of NY–ESO–1 Epitopes Presented by Human Histocompatibility Antigen (HLA)–DRB4*0101–0103 and Recognized by CD4+T Lymphocytes of Patients with NY–ESO–1–expressing Melanoma"J. Exp. Med, vol. 191, No 4, pp. 625–630 (Feb. 21, 2000).

Steven A. Rosenberg, "A New Approach to the Adoptive Immunotherapy of Cancer with Tumor–Infiltrating Lymphocytes", Science, vol. 233, pp. 1318–1321 (Sep. 19,1986).

Naoki Shimbara et al., "Contribution of Proline Residue for Efficient Production of MHC Class I Ligands by Proteasomes," The Journal of Biological Chemistry, vol. 273, No. 36, pp. 23062–23071. 1998.

Altuvia, et al., "A Structure–based algorithm to predict potential binding peptides to MHC molecules with hydrophobic binding pockets," Human Immunology, 58: 1–11 (1997).

Ayyoub, et al., "Lack of tumor recognition by hTERT peptide 540–548–specific CD8+T cells from melanoma patients reveals inefficient antigen processing," Eur. J. Immunol., 31:2642–2651 (2001).

Bettinotti, et al, "Stringent Allele/Epitope Requirements for MART–1/Melan A Immunodominance: Implications for Peptide–Based Immunotherapy," J. Immunol., 161:877–889 (1998).

Brown, et al., "Structural and serological simularity of MHC–linked LMP and proteasome (multicatalytic proteinase) complexes," Nature, 353:355–357 (1991).

Butterfield, et al., "Generation of Melanoma–Specific Cytotoxic T Lymphocytes by Dendritic Cells Tranduced with a MART–1 Adenovirus," J. Immunol., 161:5607–5613 (1998).

Chattergoon, et al., "Genetic Immunization: a new era in vaccines and immune therapeutics," FASEB J., 11:753–763 (1997).

Chaux, et al., "Identification of Five MAGE–A1 Epitopes Recognized by Cytolytic T Lymphocytes Obtained by In Vitro Stimulation with Dendritic Cells Transduced with MAGE–A1," The Journal of Immunology, 163: 2928–2936 (1999).

Davis, H. L., "Plasmid DNA expression systems for the purpose of immunization," Current Opinion in Biotechnology, 8:635–640 (1997).

Dean, D. A. et al., "Sequence requirements for plasmid nuclear import," Experimental Cell Research, 253:713–722 (1999).

Dick, et al., "Proteolytic Processing of Ovalbumin and β–galactosidase by the Proteasome to Yield Antigenic Peptides," J. Immunology, 152:3884–3894 (1994).

Farrar, et al., "The molecular cell biology of interferon–γ and its receptor," Annu. Rev. Immunol. 11:571–611 (1993).

Fiette, et al., "Theiler's virus infection of 129Sv mice that lack the interferon α/β or interferon γ receptors," J. Exp. Med., 181:2069–2076 (1995).

Gale, Jr., et al, "Evidence that Hepatitis C virus resistance to interferon is mediated through repression of the PKR protein kinase by the nonstructural 5A protein," Virology, 230:217–227 (1997).

Glynne, et al., "A proteasome–related gene between the two ABC transporter loci in the class II region of the human MHC," Nature, 353:357–360 (1991).

Gulukota, et al., "Two Complementary methods for predicting peptides binding major histocompatibility complex molecules," J. Mol. Biol., 267: 1258–1267 (1997).

Gurunathan, S. et al., "DNA vaccines: a key for inducing long–term cellular immunity," Current Opinion in Immunology, 12:422–447 (2000).

Heim, et al., "Expression of hepatitis C virus proteins inhibits signal transduction through the Jak–STAT pathway," Journal of Virology, 73(10):8469–8475 (1999).

Huang, et al., "Immune response in mice that lack the interferon–γ receptor," Science, 259:1742–1745 (1993).

International Search Report from co–pending Application No. PCT/US01/13806.

Kang, et al., "Induction of Melanoma Reactive T Cells by Stimulator Cells Expressing Melanoma Epitope–Major Histocompatibility Complex Class I Fusion Proteins," Cancer Res., 57:202–205 (1997).

Kawakami, et al., "The Use of Melanosomal Proteins in the Immunotherapy of Melanoma," J. Immunother., 21(4):237–246 (1998).

Kelly, et al., "Second proteasome–related gene in the human MHC class II region," Nature, 353:667–668 (1991).

Kittlesen, et al., "Human Melanoma Patients Recognize an HLA–A1–Restricted CTL Epitope from Tyrosinase Containing Two Cysteine Residues: Implications for Tumor Vaccine Development," J. Immunol., 160(5):2099–2106 (1998).

Kungid, T.M., et al., "On the role of antigen in maintaining cytotoxid T cell memory," Proc. Natl. Acad. Sci., 93:9716–9723 (1996).

Larregina, et al., "Direct Transfection and Activation of Human Cutaneous Dendritic Cells," Gene Ther., 8:608–617 (2001).

Leitner, et al., "DNA and RNA–based vaccines: principles, progress and prospects," Vaccine, 18:765–777 (2000).

Levy, et al., "Using ubiquitin to follow the metabolic fate of a protein," Proc. Natl. Acad. Sci USA, 93: 4907–4912 (1996).

Linette, et al., "In Vitro Priming with Adenovirus/gp100 Antigen–Transduced Dendritic Cells Reveals the Epitope Specificity of HLA–A*0201–Restricted CD8+ T Cells in Patients with Melanoma," J. Immunol., 164: 3402–3412 (2000).

Loftus, et al., "Peptides Derived from Self–Proteins as Partial Agonists and Antagonists of Human CD8+ T–cell Clones Reactive to Melanoma/Melanocyte Epitope MART1(27–35)," Cancer Res., 58: 2433–2439 (1998).

Martinez, et al., "Homology of proteasome subunits to a major histocompatibility complex–linked LMP gene," Nature, 353:664–667(1991).

Mateo, L., et al., "An HLA–A2 polyepitope vaccine for melanoma immunotherapy," Journal of Immunology, 163:4058–4063 (1999).

McCluskie et al., "Route and Method of Delivery of DNA Vaccine Influence Immune Response in Mice and Non–Human Primates," Molecular Medicine, 5:287–300 (1999).

Miconnet et al., "Amino acid identity and/or position determine the proteasomal cleavage of the HLA–A *0201–restricted peptide tumor antigen MAGE–3," The American Society for Biochemistry and Molecular Biology, Inc., pp. 1–20 (2000).

Murphy, et al., "Higher–Dose and Less Frequent Dendritic Cell Infusions with PSMA Peptides in Hormone–Refractory Metastatic Prostate Cancer Patients," *The Prostate*, 43:59–62 (2000).

Noppen, et al., "Naturally processed and concealed HLA–A2.1–restricted epitopes from tumor–associated antigen tyrosinase–related protein–2," *Int. J. Cancer.*, 82:241–246 (2000).

Nussbaum, et al., "Cleavage motifs of the yeast 20S proteasome β subunits deduced from digest of enolase 1," *Proc. Natl. Acad. Sci USA*, 95: 12504–12509 (1998).

Oehen, S., et al., "Antivirally protective cytotoxic T cell memory to lymphocytic choriomeningitis virus is governed by persisting antigen," *J. Exp Med.*, 176:1273–1281 (1992).

Pantaleo, G., et al., "Evidence for rapid disappearance of initially expanded HIV—specific $CD8^+T$ cell clones during primary HIV infection," *Proc. Natl. Acad. Sci.*, 94:9848–9853 (1997).

Parker, et al., "Scheme for ranking potential HLA–A2 binding peptides based on independent binding of individual peptide side–chains," *Journal of Immunlology*, 152: 163 (1994).

Perez–Diez, et al., "Generation of CD8+ and CD4+ T–cell Response to Dendritic Cells Genetically Engineered to Express the MART–1/Melan–A Gene," *Cancer Res.*, 58: 5305–5309 (1998).

Puccetti, P., et al., "Use of skin test assay to determine tumor–specific CD8+ T cell reactivity," *Eur. J. Immunol.*, 24:1446–1452 (1994).

Rammensee, et al., *MHC Ligands and Peptide Motifs*, (Landes Bioscence, Austin, Texas), Chapter 4, 217–369 (1997).

Raz, et al., "Preferential induction of a $Th_1$ immune response and inhibition of specific IgE antibody formation by plasmid DNA immunization," *Proc. Natl. Acad. Sci. USA*, 93: 5141–5145 (1996).

Reeves, et al., "Retroviral Transduction of Human Dendritic Cells with a Tumor–Associated Antigen Gene," *Cancer Res.*, 56: 5672–5677 (1996).

Roman, et al., "Immunostimulatory DNA sequences function as T helper–1–promoting adjuvants," *Nature Medicine*, 3: 849–854 (1997).

Rosmorduc, et al., "Inhibition of interferon–inducible MxA protein expression by hepatitis B virus capsid protein," *Journal of General Virology*, 80:1253–1262 (1999).

Ryan, et al., "A model for nonstoichiometric, cotranslation protein scission in eukaryotic ribosomes," *Bioorganic Chemistry*, 27: 55–79 (1999).

Salmi, et al., "Tumor endothelium selectively supports binding of IL–2–propagated tumor–infiltrating lymphocytes," *The Journal of Immunology*, 154:6002–6012 (1995).

Sato, et al., "Immunostimulatory DNA sequences necessary for effective intradermal gene immunization," *Science*, 273: 352–354 (1996).

Schneider, et al., "Overlapping Peptides of melanocyte differentiation antigen Melan–A/MART–1 recognized by autologous cytolytic T lymphocytes in association with HLA–B45.1 and HLA–A2.1," *Int. J. Cancer*, 75(3):451–458 (1998).

Seipelt, et al., "The structures of picornaviral proteinases," *Virus Research*, 62: 159–168 (1999).

Stauss, et al., "Induction of Cytotoxic T Lymphocytes with Peptides In Vitro: Identification of Candidate T–cell Epitopes in Human Papilloma Virus," *Proc. Natl. Acad. Sci.*, 89:7871–7875 (1992).

Sturniolo, et al., "Generation of tissue–specific and promiscuous HLA ligand databases using DNA microarrays and virtual HLA class II matrices," *Nature Biotechnology*, 17: 555–561 (1999).

Taylor, et al., "Inhibition of the interferon–inducible protein kinase PKR by HVC E2 protein," *Science*, 285:107–110 (1999).

Tjoa, et al., "Evaluation of Phase I/II Clinical Trials in Prostate Cancer with Dendritic Cells and PSMA Peptides," *Prostate*, 36:39–44 (1998).

Twu, et al., " Transcription of the human beta interferon gene is inhibited by hepatitis B virus," *Journal of Virology*, 63(7):3065–3071 (1989).

Valmori, et al., "Induction of Potent Antitumor CTL Responses by Recombinant Vaccinia Encoding a Melan–A Peptide Analogue," *J. Immunol.*, 164: 1125–1131 (2000).

Wang, et al., "Phase I Trial of a MART–1 Peptide Vaccine with Incomplete Freund's Adjuvant for Resected High–Risk Melanoma," *Clin. Cancer Res.*, 10: 2756–2765 (1999).

Yewedell et al., "MHC–encoded proteasome subunits LMP2 and LMP7 are not required for efficient antigen presentation," J. Immunology, 152:1163–1169 (1994).

Young, J. W., et al., "Dendritic cells as adjuvants for class I major histocompatibility complex–restricted antitumor immunity," *J. Exp. Med.*, 183:7–11 (1996).

Zajac, et al., "Enhanced Generation of Cytotoxic T Lymphocytes Using Recombinant Vaccinia Virus Expressing Human Tumor–Associated Antigens and B7 Costimulatory Molecules," *Cancer Res.*, 58: 4567–4571 (1998).

Zajac, et al., "Generation of Tumoricidal Cytotoxic T Lymphocytes from Healthy Donors after In Vitro Stimulation with a Replication–Incompetent Vaccinia Virus Encoding MART–1/Melan–A 27–35 Epitope," *Int. J. Cancer*, 71: 491–496 (1997).

Zhai, et al., "Antigen–Specific Tumor Vaccines: Development and Characterization of Recombinant Adenoviruses Encoding MART1 or gp100 for Cancer Therapy," *J. Immunol.*, 156:700–710 (1996).

NCBI Blast Accession Number NP_005502.

Melief, C. J., *Cancerlit*, Database Accession No. 1998625858, 1996, "Towards T–cell immunotherapy of cancer," Meeting Abstract.

Morel, et al., *Immunity*, 12:107–117, 2000, "Processing of some antigens by the standard proteasome but not by the immunoproteasome results in poor presentation by dendritic cells."

Rammensee, et al., *Immunogenetics*, 50:213–219, 1999, "SYFPEITHI: Database for MHC ligands and peptide motifs."

Rock, et al., *Annu. Rev. Immunol.*, 17:739–779, 1999, "Degradation of cell proteins and the generation of MHC class I–presented peptides."

Schirle, et al., *Journal of Immunological Methods*, 257:1–16, 2000, "Combining computer algorithms with experimental approaches permits the rapid and accurate identification of T dell epitopes from defined antigens."

Thomson, et al., *Proc. Natl. Acad. Sci. USA*, 92:5845–5849, 1995, Minimal epitopes expressed in a recombinant polyepitope protein are processed and presented to $CD8^+$cytotoxic T cells: Implications for vaccine design.

Aki, et al. Interferon–y Induces Different Subunit Organizations and Functional Diversity of Proteasomes, J. Biochem. 115, 257–269 (1994).

Arnold, et al., Proteasome subunits encoded in the MHC are not generally required for the processing of peptides bound by MHC class I molecules, Nature, vol. 360, p. 171–174 (1992).

Bachman, M.F., et al. (1994) In vitro vs. in vivo assays for the assessment of T–and B cell function, Curr. Opin. Immunol. 6:320–326.

Boes, et al., Interferon y Stimulation Modulates the Proteolytic Activity and Cleavage Site Preference of 20S Mouse Proteasomes, J. Exp. Med. vol. 179, 901–909, Mar. 1994.

DeGroot, et al., An Interactive Web Site Providing Major Histocompatibility Ligand Predictions: Application to HIV Research, Aids Res. and Human Retrov. vol. 13, Nu. 7, (1997).

Dick, et al., Coordinated Dual Cleavages Induced by the Proteasome Regulator PA28 Lead to Dominant MHC Ligands, Cell, vol. 86, 253–262, Jul. (1996).

Driscoll, et al., MHC–linked LMP gene products specifically alter peptidase activities of the proteasome, Nature, vol. 365, Sep. (1993).

Durrant LG, (1997) Cancer vaccines, Anti–cancer drugs, 8:727–733.

Gaczynska, Maria, et al., y–Interferon and expression of MHC genes regulate peptide hydrolysis by proteasomes, Nature, vol. 365, Sep. (1993).

Gileadi, et al., Generation of an Immunodominant CTL Epitope is Affected by Proteasome Subunit Composition and Stability of the Antigenic Protein, p. 6045–6052 (1999) J. Immunology vol. 163.

Groettrup. et al., A role for the proteasome regulator PA28a in antigen presentation, Nature, vol. 381, May (1996) pp. 166–168.

Jäger, E., et al., (1996) Granulocyte–macrophage–colony–stimulating factor enhances immune responses to melanoma–associated peptides in vivo, Int. J. Cancer 67:54–62.

Jäger E. et al., (1998) Simultaneous humoral and cellular immune response against cancer–testis antigen NY–ESO–1: definition of human histocompatibility leukocyte antigen (HLA)–A2–binding Peptide Epitopes 187:265–270.

Kündig, T.M. et al. (1995) Fibroblasts as efficient antigen–presenting cells in lymphoid organs, Proc. Natl. Acad. Sci. 268:1343–1347.

Lee, et al., Characterization of circulating T cells specific for tumor–associated antigens in melanoma patients, Nature Medicine, vol. 5, Jun. (1999).

Maksymowych, et al., Invasion by *Salmonella typhimurium* Induces Increased Expression of the LMP, MECL, and PA28 Proteasome Genes and Changes in the Peptide Repertoire of HLA–B27, Infection and Immunity, p. 4624–4632, (1998).

Meister, et al., Two novel T cell epitope prediction algorithms based on MHC–binding motifs; comparison of predicted and published epitopes from Mycobacterium tuberculosis and HIV protein sequences, Vaccine, vol. 13, p. 581–591, (1995).

Missale, et al., HLA–A31– and HLA–Aw68–restricted Cytotoxic T cell Responses to a Single Hepatitis B Virus Nucelocapsid Epitope during Acute Viral Hepatitis, J. Exp. Med. p. 751–762, vol. 177, Mar. (1993).

Momburg, et al., Proteasome subunits encoded by the major histocompatibility complex are not essential for antigen presentation, Nature, vol. 360, Nov. (1992).

Moskophidis D. et al., (1995) Immunobiology of Cytotoxid T–cell escape mutants of lymphocytic choriomentingitis virus, Journal of Virology, 69:2187–2793.

Oldstone, M.B et al., (1995) Discriminated selection among viral peptides with the appropriate anchor residues: Implications for the size of the cytotoxic T–lymphocyte repertoire and control of viral infection, Journal of Virology, 69:7423–7429.

Ortiz–Navarrette, et al., Subunit of the '20S proteasome (multicatalyic proteinase)encoded by the major histocompatibility complex, Nature, vol. 353, Oct. (1991).

Preckel, et al., Impaired Immunoproteasome Assembly and Immune Responses in PA28–I–Mice, Science, vol. 286 Dec. (1999).

Rammensee, H.G. et al., (1997) MHC ligands and peptide motifs: first listing, Immunogenetics 41:178–228.

Rehermann, et al., The Cytotoxic T Lymphocyte Response to Multiple Hepatitis B Virus Polymerase Epitopes During and After Acute Viral Hepatitis, Jr. of Exp. Medicine, vol. 181, p. 1047–1058 Mar. 1995.

Roberts, et al., Prediction of HIV Peptide Epitopes by a Novel Algorithm, Aids Research and Human Retroviruses, vol. 12, p. 593–610, (1996).

Sewell, et al., IFM–y Exposes a Cryptic Cytoxic T Lymphocyte Epitope in HIV–1 Reverse Transcriptase, Am. Assoc. of Immunol. p. 7075–7079, (1999).

Sijts, et al., Efficient Generation of a Hepatitis B Virus Cytotoxic T Lymphocyte Epitope Requires the Structural Features of Immunoproteasomes J. Exp. Med. vol. 191, No. 3, p. 503–513 Feb. (2000).

Speiser, D.E. et al., (1997) Self antigens expressed by solid tumors do not efficiently stimulate naive or activated T cells: implications for immunotheraphy, J. Exp. Med. 186:645–653.

Steinman R.M. et al., (1991) The dendritic cell system and its role in immunogenicity, Annual Review of Immunology 9:271–96.

Van Kaer, et al., Altered Peptidase and Viral–Specific T Cell Response in LMP2 Mutant Mice, Immunity, vol. 1, 533–541, Oct. (1994).

Vitiello, et al., Comparison of Cytotoxic T lymphocyte responses induced by peptide or DNA immunization: implications on immunogenicity and immunodominance, Euro. Jr. Immunol. p. 671–678 (1997).

Yang, et al., Proteasomes are regulated by interferon y: Implications for antigen processing, Proc. Natl. Acadm. Sci., vol. 89, p. 4928–4932, Jun. (1992).

Zipkin I., (1998) Cancer vaccines, Bio Century 6:A1–A6.

Van den Eynde, et al., 2001, *Current Opinion in Immunology*, 13:147–153.

* cited by examiner

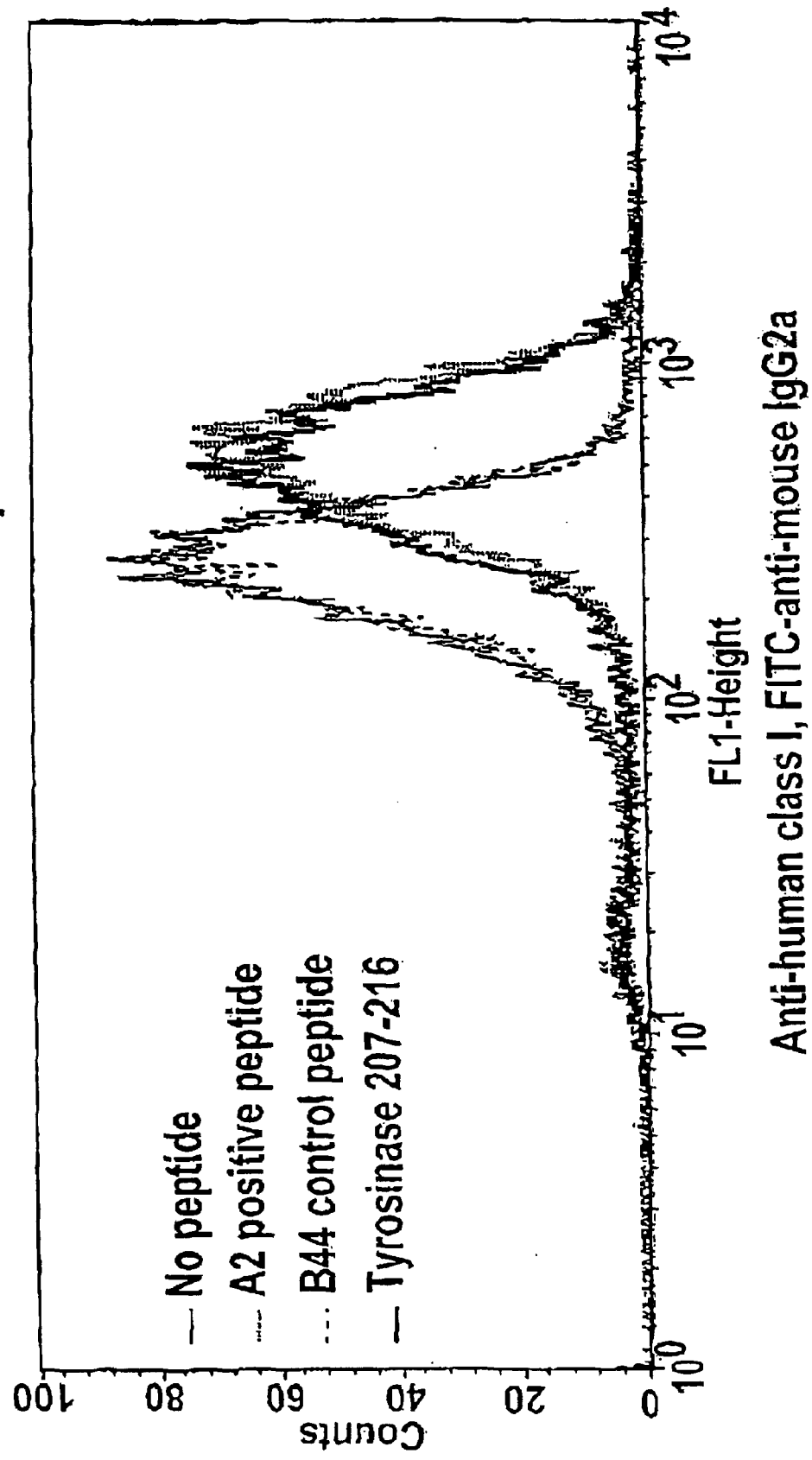

METHOD OF EPITOPE DISCOVERY

BACKGROUND OF THE INVENTION

1. Field of the Invention

The invention disclosed below relates to the identification of target cell antigens that can be used to generate immunologically active compositions. These compositions, when administered, will stimulate the immune system of a subject to mount an immune response against a target cell displaying the target antigen. The invention is contemplated to have utility in the treatment and prevention of neoplastic and viral disease.

2. Description of the Related Art

Neoplasia and the Immune System

The neoplastic disease state commonly known as cancer is thought to generally result from a single cell growing out of control. The uncontrolled growth state typically results from a multi-step process in which a series of cellular systems fail, resulting in the genesis of a neoplastic cell. The resulting neoplastic cell rapidly reproduces itself, forms one or more tumors, and eventually may cause the death of the host.

Because the progenitor of the neoplastic cell shares the host's genetic material, neoplastic cells are largely exempt from the host's immune system. During immune surveillance, the process in which the host's immune system surveys and localizes foreign materials, a neoplastic cell will appear to the host's immune surveillance machinery as a "self" cell.

Viruses and the Immune System

In contrast to cancer cells, virus infection involves the expression of clearly non-self antigens. As a result, many virus infections are successfully dealt with by the immune system with minimal clinical sequela. Moreover, it has been possible to develop effective vaccines for many of those infections that do cause serious disease. A variety of vaccine approaches have been successfully used to combat various diseases. These approaches include subunit vaccines consisting of individual proteins produced through recombinant DNA technology. Notwithstanding these advances, the selection and effective administration of minimal epitopes for use as viral vaccines has remained problematic.

In addition to the difficulties involved in epitope selection stands the problem of viruses that have evolved the capability of evading a host's immune system. Many viruses, especially viruses that establish persistent infections, such as members of the herpes and pox virus families, produce immunomodulatory molecules that permit the virus to evade the host's immune system. The effects of these immunomodulatory molecules on antigen presentation may be overcome by the targeting of select epitopes for administration as immunogenic compositions. To better understand the interaction of neoplastic cells and virally infected cells with the host's immune system, a discussion of the system's components follows below.

The immune system functions to discriminate molecules endogenous to an organism ("self" molecules) from material exogenous or foreign to the organism ("non-self" molecules). The immune system has two types of adaptive responses to foreign bodies based on the components that mediate the response: a humoral response and a cell-mediated response. The humoral response is mediated by antibodies, while the cell-mediated response involves cells classified as lymphocytes. Recent anticancer and antiviral strategies have focused on mobilizing the host immune system as a means of anticancer or antiviral treatment or therapy.

The immune system functions in three phases to protect the host from foreign bodies: the cognitive phase, the activation phase, and the effector phase. In the cognitive phase, the immune system recognizes and signals the presence of a foreign antigen or invader in the body. The foreign antigen can be, for example, a cell surface marker from a neoplastic cell or a viral protein. Once the system is aware of an invading body, antigen specific cells of the immune system proliferate and differentiate in response to the invader-triggered signals. The last stage is the effector stage in which the effector cells of the immune system respond to and neutralize the detected invader.

An array of effector cells implement an immune response to an invader. One type of effector cell, the B cell, generates antibodies targeted against foreign antigens encountered by the host. In combination with the complement system, antibodies direct the destruction of cells or organisms bearing the targeted antigen. Another type of effector cell is the natural killer cell (NK cell), a type of lymphocyte having the capacity to spontaneously recognize and destroy a variety of virus infected cells as well as malignant cell types. The method used by NK cells to recognize target cells is poorly understood.

Another type of effector cell, the T cell, has members classified into three subcategories, each playing a different role in the immune response. Helper T cells secrete cytokines which stimulate the proliferation of other cells necessary for mounting an effective immune response, while suppressor T cells down-regulate the immune response. A third category of T cell, the cytotoxic T cell (CTL), is capable of directly lysing a targeted cell presenting a foreign antigen on its surface.

The Major Histocompatibility Complex and T Cell Target Recognition

T cells are antigen specific immune cells that function in response to specific antigen signals. B lymphocytes and the antibodies they produce are also antigen specific entities. However, unlike B lymphocytes, T cells do not respond to antigens in a free or soluble form. For a T cell to respond to an antigen, it requires the antigen to be bound to a presenting complex known as the major histocompatibility complex (MHC).

MHC complex proteins provide the means by which T cells differentiate native or "self" cells from foreign cells. There are two types of MHC, class I MHC and class II MHC. T Helper cells (CD4$^+$) predominately interact with class II MHC proteins while cytolytic T cells (CD8$^+$) predominately interact with class I MHC proteins. Both MHC complexes are transmembrane proteins with a majority of their structure on the external surface of the cell. Additionally, both classes of MHC have a peptide binding cleft on their external portions. It is in this cleft that small fragments of proteins, native or foreign, are bound and presented to the extracellular environment.

Cells called antigen presenting cells (APCs) display antigens to T cells using the MHC complexes. For T cells to recognize an antigen, it must be presented on the MHC complex for recognition. This requirement is called MHC restriction and it is the mechanism by which T cells differentiate "self" from "non-self" cells. If an antigen is not displayed by a recognizable MHC complex, the T cell will not recognize and act on the antigen signal. T cells specific for the peptide bound to a recognizable MHC complex bind to these MHC-peptide complexes and proceed to the next stages of the immune response.

As discussed above, neoplastic cells are largely ignored by the immune system. A great deal of effort is now being expended in an attempt to harness a host's immune system to aid in combating the presence of neoplastic cells in a host. One such area of research involves the formulation of anticancer vaccines.

Anticancer Vaccines

Among the various weapons available to an oncologist in the battle against cancer is the immune system of the patient. Work has been done in various attempts to cause the immune system to combat cancer or neoplastic diseases. Unfortunately, the results to date have been largely disappointing. One area of particular interest involves the generation and use of anticancer vaccines.

To generate a vaccine or other immunogenic composition, it is necessary to introduce to a subject an antigen or epitope against which an immune response may be mounted. Although neoplastic cells are derived from and therefore are substantially identical to normal cells on a genetic level, many neoplastic cells are known to present tumor-associated antigens (TuAAs). In theory, these antigens could be used by a subject's immune system to recognize these antigens and attack the neoplastic cells. Unfortunately, neoplastic cells appear to be ignored by the host's immune system.

A number of different strategies have been developed in an attempt to generate vaccines with activity against neoplastic cells. These strategies include the use of tumor associated antigens as immunogens. For example, U.S. Pat. No. 5,993,828, describes a method for producing an immune response against a particular subunit of the Urinary Tumor Associated Antigen by administering to a subject an effective dose of a composition comprising inactivated tumor cells having the Urinary Tumor Associated Antigen on the cell surface and at least one tumor associated antigen selected from the group consisting of GM-2, GD-2, Fetal Antigen and Melanoma Associated Antigen. Accordingly, this patent describes using whole, inactivated tumor cells as the immunogen in an anticancer vaccine.

Another strategy used with anticancer vaccines involves administering a composition containing isolated tumor antigens. In one approach, MAGE-A1 antigenic peptides were used as an immunogen. (See Chaux, P., et al., "Identification of Five MAGE-A1 Epitopes Recognized by Cytolytic T Lymphocytes Obtained by In Vitro Stimulation with Dendritic Cells Transduced with MAGE-A1," J. Immunol., 163(5):2928–2936 (1999)). There have been several therapeutic trials using MAGE-A1 peptides for vaccination, although the effectiveness of the vaccination regimes was limited. The results of some of these trials are discussed in Vose, J. M., "Tumor Antigens Recognized by T Lymphocytes," 10$^{th}$ European Cancer Conference, Day 2, Sep. 14, 1999.

In another example of tumor associated antigens used as vaccines, Scheinberg, et al. treated 12 chronic myelogenous leukemia (CML) patients already receiving interferon (IFN) or hydroxyurea with 5 injections of class I-associated bcr-abl peptides with a helper peptide plus the adjuvant QS-21. Scheinberg, D. A., et al, "BCR-ABL Breakpoint Derived Oncogene Fusion Peptide Vaccines Generate Specific Immune Responses in Patients with Chronic Myelogenous Leukemia (CML) [Abstract 1665], American Society of Clinical Oncology 35$^{th}$ Annual Meeting, Atlanta (1999). Proliferative and delayed type hypersensitivity (DTH) T cell responses indicative of T-helper activity were elicited, but no cytolytic killer T cell activity was observed within the fresh blood samples.

Additional examples of attempts to identify TAAs for use as vaccines are seen in the recent work of Cebon, et al. and Scheibenbogen, et al. Cebon et al. Immunized patients with metastatic melanoma using intradermally administered MART-1$_{26-35}$ peptide with IL-12 in increasing doses given either subcutaneously or intravenously. Of the first 15 patients, 1 complete remission, 1 partial remission, and 1 mixed response were noted. Immune assays for T cell generation included DTH, which was seen in patients with or without IL-12. Positive CTL assays were seen in patients with evidence of clinical benefit, but not in patients without tumor regression. Cebon, et al., "Phase I Studies of Immunization with Melan-A and IL-12 in HLA A2+Positive Patients with Stage III and IV Malignant Melanoma," [Abstract 1671], American Society of Clinical Oncology 35$^{th}$ Annual Meeting, Atlanta (1999).

Scheibenbogen, et al. immunized 18 patients with 4 HLA class I restricted tyrosinase peptides, 16 with metastatic melanoma and 2 adjuvant patients. Scheibenbogen, et al., "Vaccination with Tyrosinase peptides and GM-CSF in Metastatic Melanoma: a Phase II Trial," [Abstract 1680], American Society of Clinical Oncology 35$^{th}$, Annual Meeting, Atlanta (1999). Increased CTL activity was observed in 4/15 patients, 2 adjuvant patients, and 2 patients with evidence of tumor regression. As in the trial by Cebon et al., patients with progressive disease did not show boosted immunity. In spite of the various, efforts expended to date to generate efficacious anticancer vaccines, no such composition has yet been developed.

Vaccine strategies to protect against viral diseases have had many successes. Perhaps the most notable of these is the progress that has been made against the disease small pox, which has been driven to extinction. The success of the polio vaccine is of a similar magnitude.

Viral vaccines can be grouped into three classifications: live attenuated virus vaccines, such as vaccinia for small pox, the Sabin poliovirus vaccine, and measles mumps and rubella; whole killed or inactivated virus vaccines, such as the Salk poliovirus vaccine, hepatitis A virus vaccine and the typical influenza virus vaccines; and subunit vaccines, such as hepatitis B. Due to their lack of a complete viral genome, subunit vaccines offer a greater degree of safety than those based on whole viruses.

The paradigm of a successful subunit vaccine is the recombinant hepatitis B vaccine based on the viruses envelope protein. Despite much academic interest in pushing the subunit concept beyond single proteins to individual epitopes the efforts have yet to bear much fruit. Viral vaccine research has also concentrated on the induction of an antibody response although cellular responses also occur. However, many of the subunit formulations are particularly poor at generating a CTL response.

SUMMARY OF THE INVENTION

The invention disclosed herein is directed to the identification of epitopes that are useful for generating vaccines capable of inducing an immune response from a subject to whom the compositions have been administered. One embodiment of the invention relates to a method of epitope discovery comprising the step of selecting an epitope from a population of peptide fragments of an antigen associated with a target cell, wherein the fragments have a known or predicted affinity for a major histocompatibility complex class I receptor peptide binding cleft, wherein the epitope selected corresponds to a proteasome cleavage product of the target cell.

Another embodiment of the invention relates to a method of discovering an epitope comprising the steps of: providing a sequence from a target cell, wherein the sequence encodes or comprises a protein expressed in the target cell; identifying a population of peptide fragments of the protein, wherein members of the population of peptide fragments have a known or predicted affinity for a major histocompatibility complex class I receptor peptide binding cleft; selecting the epitope from the population of peptide fragments, wherein the epitope corresponds to a product of a proteasome active in the target cell.

One aspect of this embodiment relates an epitope discovered by the aforementioned method. Another aspect of this embodiment relates to a vaccine comprising the discovered epitope. Still another aspect of the invention relates to a method of treating an animal, comprising administering to the animal the aforementioned vaccine.

One embodiment of the disclosed invention relates to a method of epitope discovery comprising the steps of: providing a neoplastic cell and a sequence, wherein the sequence comprises or encodes an antigen associated with the neoplastic cell; identifying a population of peptide fragments of the antigen, wherein the population of peptide fragments is predicted to have an affinity for a major histocompatibility complex class I receptor peptide binding cleft; selecting an epitope from the population of peptide fragments, wherein the epitope is determine by in vitro analysis to be a proteasome cleavage reaction product of a proteasome active in the neoplastic cell.

One aspect of this embodiment relates an epitope discovered by the aforementioned method. Another aspect of this embodiment relates to a vaccine comprising the discovered epitope. Still another aspect of the invention relates to a method of treating an animal, comprising administering to the animal the aforementioned vaccine.

Another embodiment of the disclosed invention relates to a method of epitope discovery comprising the step of selecting an epitope from a population of peptide fragments of an antigen associated with a target in a host, wherein the fragments have a known or predicted affinity for a major histocompatibility complex class II receptor peptide binding cleft of the host, wherein the epitope selected corresponds to a product of proteolytic cleavage of the antigen in a cell of the host.

One aspect of this embodiment relates an epitope discovered by the aforementioned method. Another aspect of this embodiment relates to a vaccine comprising the discovered epitope. Still another aspect of the invention relates to a method of treating an animal, comprising administering to the animal the aforementioned vaccine.

BRIEF DESCRIPTION OF THE DRAWINGS

FIG. 3 depicts the results of a flow cytometry assay verifying HLA binding by Tyrosinase peptide 207–216.

DETAILED DESCRIPTION OF THE PREFERRED EMBODIMENTS

Figure 1:
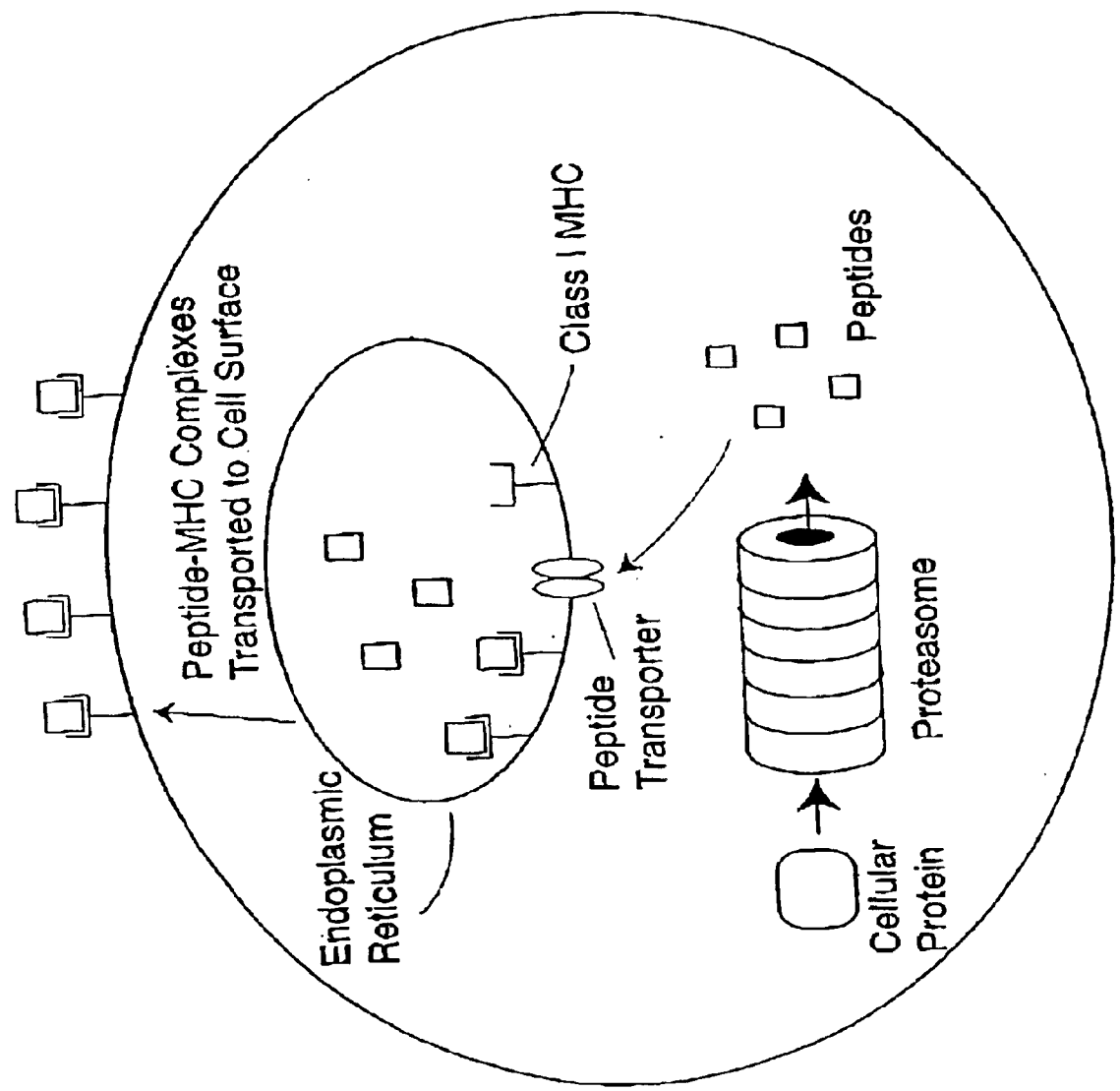
FIG. 1 depicts schematically the parts of a cell involved in protein processing by the proteasome and epitope presentation.

Embodiments of the invention disclosed herein provide methods for identifying epitopes of target antigens that can be used to generate immunologically effective vaccines. Such vaccines can stimulate the immune system to recognize and destroy target cells displaying the selected epitopes. Embodiments of the invention are particularly useful in the treatment and prevention of cancers and of infections of cells by intracellular parasites, as well as in the treatment or prevention of conditions associated with other pathogens, toxins, and allergens.

Certain kinds of targets are particularly elusive to the immune system. Among these are many kinds of cancer, as well as cells infected by intracellular parasites, such as, for example, viruses, bacteria, and protozoans. A great deal of research has been done to identify useful antigens and epitopes for generating an effective immune response against such targets, with little success. This disclosure provides a basis for the efficient discovery of a new generation of effective epitopes effective against such elusive targets.

The invention disclosed herein makes it possible to select epitope sequences with true biological relevance. For an epitope to have biological significance, e.g., to function in stimulating an immune response, it must have an affinity for the binding cleft of a major histocompatibility complex (MHC) receptor peptide. There are various means, known in the art, of predicting whether an oligopeptide sequence will have an MHC binding affinity. However, most of the sequences predicted to have MHC binding affinity are not biologically relevant, because they are not actually presented on the surface of a target cell or a pAPC.

The methods of the disclosed invention permit the vaccine designer to ignore peptides that, despite predicted high binding affinity for MHC, will never be useful because they cannot be presented by target cells. Accordingly, methods and teachings disclosed herein provide a major advance in vaccine design, one that combines the power of antigen sequence analysis with the fundamental realities of immunology. The methods taught herein allows for the simple and effective selection of meaningful epitopes for creation of MHC class I or class II vaccines using any polypeptide sequence corresponding to a desired target.

Definitions

Unless otherwise clear from the context of the use of a term herein, the following listed terms shall generally have the indicated meanings for purposes of this description.

PROFESSIONAL ANTIGEN-PRESENTING CELL (pAPC)— a cell that possesses T cell costimulatory molecules and is able to induce a T cell response. Well characterized pAPCs include dendritic cells, B cells, and macrophages.

PERIPHERAL CELL—a cell that is not a pAPC.

HOUSEKEEPING PROTEASOME—a proteasome normally active in peripheral cells, and generally not present or not strongly active in pAPCs.

IMMUNE PROTEASOME—a proteasome normally active in pAPCs; the immune proteasome is also active in some peripheral cells in infected tissues.

EPITOPE—a molecule or substance capable of stimulating an immune response. In preferred embodiments, epitopes according to this definition include but are not necessarily limited to a polypeptide and a nucleic acid encoding a polypeptide, wherein the polypeptide is capable of stimulating an immune response. In other preferred embodiments, epitopes according to this definition include but are not necessarily limited to peptides presented on the surface of cells non-covalently bound to the binding cleft of class I MHC, such that they can interact with T cell receptors.

MHC EPITOPE—a polypeptide having a known or predicted binding affinity for a mammalian class I or class II major histocompatibility complex (MHC) molecule.

HOUSEKEEPING EPITOPE—In a preferred embodiment, a housekeeping epitope is defined as a polypeptide fragment that is an MHC epitope, and that is displayed on a cell in which housekeeping proteasomes are predominantly active. In another preferred embodiment, a housekeeping epitope is defined as a polypeptide containing a housekeeping epitope according to the foregoing definition, that is flanked by one to several additional amino acids. In another preferred embodiment, a housekeeping epitope is defined as a nucleic acid that encodes a housekeeping epitope according to the foregoing definitions.

IMMUNE EPITOPE—In a preferred embodiment, an immune epitope is defined as a polypeptide fragment that is an MHC epitope, and that is displayed on a cell in which immune proteasomes are predominantly active. In another preferred embodiment, an immune epitope is defined as a polypeptide containing an immune epitope according to the foregoing definition, that is flanked by one to several additional amino acids. In another preferred embodiment, an immune epitope is defined as a polypeptide including an epitope cluster sequence, having at least two polypeptide sequences having a known or predicted affinity for a class I MHC. In yet another preferred embodiment, an immune epitope is defined as a nucleic acid that encodes an immune epitope according to any of the foregoing definitions.

TARGET CELL—a cell to be targeted by the vaccines and methods of the invention. Examples of target cells according to this definition include but are not necessarily limited to: a neoplastic cell and a cell harboring an intracellular parasite, such as, for example, a virus, a bacterium, or a protozoan.

TARGET-ASSOCIATED ANTIGEN (TAA)—a protein or polypeptide present in a target cell.

TUMOR-ASSOCIATED ANTIGENS (TuAA)—a TAA, wherein the target cell is a neoplastic cell.

HLA EPITOPE—a polypeptide having a known or predicted binding affinity for a human class I or class II HLA complex molecule.

Note that the following discussion sets forth the inventor's understanding of the operation of the invention. However, it is not intended that this discussion limit the patent to any particular theory of operation not set forth in the claims.

Proteolytic Processing of Antigens

Epitopes that are displayed by MHC on target cells or on pAPCs are cleavage products of larger protein antigen precursors. For MHC I epitopes, protein antigens are digested by proteasomes resident in the cell. Intracellular proteasomal digestion typically produces peptide fragments of about 3 to 23 amino acids in length. Additional proteolytic activities within the cell, or in the extracellular milieu, can trim and process these fragments further. Processing of MHC II epitopes occurs via intracellular proteases from the lysosomal/endosomal compartment. See FIG. 1.

Presumably, most products of protein processing by proteasomes or other protease activities have little or no affinity for the binding cleft of a particular MHC receptor peptide. However, the processing products that do have such an affinity are likely to be presented, at some level of abundance, by MHC at the cell surface. Conversely, if a given oligopeptide sequence does not emerge intact from the antigen processing activities of the cell, it cannot be presented at the cell surface, regardless of the predicted affinity of the sequence for MHC.

Vaccine design that focuses entirely on MHC affinity is fundamentally flawed. The mere fact that a peptide hare MHC binding affinity does not ensure that such a peptide will make for a functional immunogen. To provide an epitope capable of eliciting an effective immune response against a TAA, the peptide must have MHC binding affinity and be the product of cellular peptide generating systems. The methods of the disclosed invention utilize both MHC binding affinity analysis and antigen processing analysis protocols to identify new epitopes of interest.

Correlating Predicted or Known MHC Binding with Proteolytic Processing of Antigens To identify epitopes potentially effective as immunogenic compounds, predictions of MHC binding alone are insufficient. Embodiments of the invention combine an analysis of MHC binding with an analysis of proteolytic processing to identify epitopes that have both of the essential properties of a useful epitope: MHC affinity and correct proteolytic processing. Peptides having both of these properties are strong candidates for vaccines and immunotherapies. Peptides lacking either of these properties are unlikely to have any significant opportunity to function as effective epitopes.

Embodiments of the invention are capable of identifying epitopes derived from TAAs for use in vaccines. The target antigens can be derived from neoplastic cells, cells infected with a virus or other intracellular parasite, or cells infected with other pathogenic agents such as bacteria, fungi, fungi, protozoans, or prions; or from other pathogenic agents such as toxins, venoms, allergens; and the like. In short, embodiments of the method can be applied to virtually any protein sequence, to identify therein epitopes capable of generation by proteolysis and capable of binding to MHC. Accordingly, the invention is not limited to any particular target or medical condition, but instead encompasses discovery of biologically relevant MHC epitopes from any useful source.

In a preferred embodiment, the TAA is characteristic of a neoplastic cell and is thus defined as a tumor-associated antigen (TuAA). Preferred TuAAs include: differentiation antigens such as MelanA (MART-1), gp 100 (Pmel 17), tyrosinase, TRP-1, TRP-2, MAGE-1, MAGE-3, BAGE, GAGE-1, GAGE-2, p15; overexpressed embryonic antigens generally; overexpressed oncogenes and mutated tumor-suppressor genes such as p53, Ras, HER-2/neu; unique tumor antigens resulting from chromosomal translocations such as BCR-ABL, E2A-PRL, H4-RET, IGH-IGK, MYL-RAR1 and viral antigens, such as Epstein Barr virus antigens (EBVA) and the human papillomavirus (HPV) antigens E6 and E7. Other antigens of interest include prostate specific antigen (PSA), prostate stem cell antigen (PSCA), MAAT-1, GP-100, TSP-180, MAGE-4, MAGE-5, MAGE-6, RAGE, p185erbB-2, p185erbB-3, c-met, nm-23H1, TAG-72, CA 19-9, CA 72-4, CAM 17.1, NuMa, K-ras, β-Catenin, CDK4, Mum-1, p15, and p16. Other target antigens are also contemplated.

A variety of methods are available and well known in the art to identify TuAAs. Examples of these techniques include differential hybridization, including the use of microarrays; subtractive hybridization cloning; differential display, either at the level of mRNA or protein expression; EST sequencing; and SAGE (sequential analysis of gene expression). These nucleic acid techniques have been reviewed by Carulli, J. P. et al J. Cellular Biochem Suppl. 30/31:286–296, 1998 (hereby incorporated by reference in its entirety). Differential display of proteins involves, for example, comparison of two-dimensional polyacrylamide gel electrophoresis of cell lysates from tumor and normal tissue, location of protein spots unique or overexpressed in the tumor, recovery of the protein from the gel, and identification of the protein using traditional biochemical or mass spectrometry sequencing techniques. An additional technique for identification of TuAAs is the SEREX technique, discussed in Türeci, O., Sahin, U., and Pfreundschuh, M., "Serological analysis of human tumor antigens: molecular definition and implications", *Molecular Medicine Today*, 3:342, 1997, and hereby incorporated by reference in its entirety. Use of these and other methods provides one of skill in the art the techniques necessary to identify useful antigens for generating housekeeping and immune class I epitopes, as well as class II epitopes for a vaccines. However, it is not necessary, in practicing the invention, to identify a novel TuAA or TAA. Rather, embodiments of the invention make it possible to identify useful epitopes from any relevant protein sequence, whether the sequence is already known or novel.

Analysis of TAA Fragments for MHC Binding

In order to identify biologically relevant epitopes, fragments within the TAA with a known or predicted affinity for MHC are identified. The amino acid sequence of a TAA can be analyzed by a number of different techniques with which to identify peptide fragments having a known or predicted affinity for the MHC peptide binding cleft. In one embodiment of the invention, TAA fragments are analyzed for their predicted ability to bind to the MHC peptide binding cleft using a computer algorithm. Each allele of MHC specifies a particular epitope binding domain. Thus, for any given MHC allele, the candidate peptides can be screened for predicted affinity thereto.

Examples of suitable computer algorithms for this purpose include that found at the world wide web page of Hans-Georg Rammensee, Jutta Bachmann, Niels Emmerich, Stefan Stevanovic: SYFPEITHI: An Internet Database for MHC Ligands and Peptide Motifs (accessible by hypertext transfer protocol (http://) at 134.2.96.221/scripts/hlaserver.dll/EpPredict.htm). Results obtained from this method are discussed in Rammensee, et al., "MHC Ligands and Peptide Motifs," Landes Bioscience Austin, Tex., 224–227, 1997, which is hereby incorporated by reference in its entirety. Another site of interest is BIMAS (accessible by hypertext transfer protocol (http://) at bimas.dcrt.nih.gov/molbio/hla_bind), which also contains a suitable algorithm.

The methods of this web site are discussed in Parker, et al., "Scheme for ranking potential HLA-A2 binding peptides based on independent binding of individual peptide sidechains," J. Immunol. 152:163–175, which is hereby incorporated by reference in its entirety.

Using the Parker, et al. derived algorithm with the methods of the invention would select peptides using a number of possible retention times (i.e. half times of dissociation) to indicate a binding sequence. In one embodiment, peptides with an infinite retention time would be selected. In another embodiment, peptides with a retention time of 25 minutes or more would be selected to indicate a binding sequence. In still another embodiment, a retention time of 15 minutes or more would be selected to indicate a binding sequence. In still another embodiment, a retention time of 10 minutes or more would be selected to indicate a binding sequence. Retention times of 9, 8, 7, 6, 5, 4, 3, 2, and 1 minute are also contemplated.

As an alternative to predictive algorithms, a number of standard in vitro receptor binding affinity assays are available to identify peptides having an affinity for a particular allele of MHC. Accordingly, by the method of this aspect of the invention, the initial population of peptide fragments can be narrowed to include only those peptides having an actual or predicted affinity for the selected allele of MHC.

Initially, peptide candidates for this analysis can include every possible sequence of about 6 to 24 contiguous amino acids from the entire protein sequence of the TAA. In a preferred embodiment, the sequences can be from about 7 to 20 amino acids in length. In a more preferred embodiment, the sequences can be from about 8 to 15 amino acids in length. For sequence analysis to identify fragments with predicted affinity for MHC 1, a most preferred embodiment analyzes all possible sequences of 9 or 10 contiguous amino acid fragments of the TAA. Analysis of the MHC affinity of the fragments can be conducted in vitro or via computer analysis of the fragments.

Selected common alleles of MHC I, and their approximate frequencies, are reported in the tables below.

TABLE 1

Estimated gene frequencies of HLA-A antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |
| A1 | 15.1843 | 0.0489 | 5.7256 | 0.0771 | 4.4818 | 0.0846 | 7.4007 | 0.0978 | 12.0316 | 0.2533 |
| A2 | 28.6535 | 0.0619 | 18.8849 | 0.1317 | 24.6352 | 0.1794 | 28.1198 | 0.1700 | 29.3408 | 0.3585 |
| A3 | 13.3890 | 0.0463 | 8.4406 | 0.0925 | 2.6454 | 0.0655 | 8.0789 | 0.1019 | 11.0293 | 0.2437 |
| A28 | 4.4652 | 0.0280 | 9.9269 | 0.0997 | 1.7657 | 0.0537 | 8.9446 | 0.1067 | 5.3856 | 0.1750 |
| A36 | 0.0221 | 0.0020 | 1.8836 | 0.0448 | 0.0148 | 0.0049 | 0.1584 | 0.0148 | 0.1545 | 0.0303 |
| A23 | 1.8287 | 0.0181 | 10.2086 | 0.1010 | 0.3256 | 0.0231 | 2.9269 | 0.0628 | 1.9903 | 0.1080 |
| A24 | 9.3251 | 0.0395 | 2.9668 | 0.0560 | 22.0391 | 0.1722 | 13.2610 | 0.1271 | 12.6613 | 0.2590 |
| A9 unsplit | 0.0809 | 0.0038 | 0.0367 | 0.0063 | 0.0858 | 0.0119 | 0.0537 | 0.0086 | 0.0356 | 0.0145 |
| A9 total | 11.2347 | 0.0429 | 13.2121 | 0.1128 | 22.4505 | 0.1733 | 16.2416 | 0.1382 | 14.6872 | 0.2756 |
| A25 | 2.1157 | 0.0195 | 0.4329 | 0.0216 | 0.0990 | 0.0128 | 1.1937 | 0.0404 | 1.4520 | 0.0924 |
| A26 | 3.8795 | 0.0262 | 2.8284 | 0.0547 | 4.6628 | 0.0862 | 3.2612 | 0.0662 | 2.4292 | 0.1191 |
| A34 | 0.1508 | 0.0052 | 3.5228 | 0.0610 | 1.3529 | 0.0470 | 0.4928 | 0.0260 | 0.3150 | 0.0432 |
| A43 | 0.0018 | 0.0006 | 0.0334 | 0.0060 | 0.0231 | 0.0062 | 0.0055 | 0.0028 | 0.0059 | 0.0059 |
| A66 | 0.0173 | 0.0018 | 0.2233 | 0.0155 | 0.0478 | 0.0089 | 0.0399 | 0.0074 | 0.0534 | 0.0178 |
| A10 unsplit | 0.0790 | 0.0038 | 0.0939 | 0.0101 | 0.1255 | 0.0144 | 0.0647 | 0.0094 | 0.0298 | 0.0133 |
| A10 total | 6.2441 | 0.0328 | 7.1348 | 0.0850 | 6.3111 | 0.0993 | 5.0578 | 0.0816 | 4.2853 | 0.1565 |
| A29 | 3.5796 | 0.0252 | 3.2071 | 0.0582 | 1.1233 | 0.0429 | 4.5156 | 0.0774 | 3.4345 | 0.1410 |
| A30 | 2.5067 | 0.0212 | 13.0969 | 0.1129 | 2.2025 | 0.0598 | 4.4873 | 0.0772 | 2.5314 | 0.1215 |
| A31 | 2.7386 | 0.0221 | 1.6556 | 0.0420 | 3.6005 | 0.0761 | 4.8328 | 0.0800 | 6.0881 | 0.1855 |
| A32 | 3.6956 | 0.0256 | 1.5384 | 0.0405 | 1.0331 | 0.0411 | 2.7064 | 0.0604 | 2.5521 | 0.1220 |
| A33 | 1.2080 | 0.0148 | 6.5607 | 0.0822 | 9.2701 | 0.1191 | 2.6593 | 0.0599 | 1.0754 | 0.0796 |
| A74 | 0.0277 | 0.0022 | 1.9949 | 0.0461 | 0.0561 | 0.0096 | 0.2027 | 0.0167 | 0.1068 | 0.0252 |

TABLE 1-continued

Estimated gene frequencies of HLA-A antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |
| A19 unsplit | 0.0567 | 0.0032 | 0.2057 | 0.0149 | 0.0990 | 0.0128 | 0.1211 | 0.0129 | 0.0475 | 0.0168 |
| A19 total | 13.8129 | 0.0468 | 28.2593 | 0.1504 | 17.3846 | 0.1555 | 19.5252 | 0.1481 | 15.8358 | 0.2832 |
| AX | 0.8204 | 0.0297 | 4.9506 | 0.0963 | 2.9916 | 0.1177 | 1.6332 | 0.0878 | 1.8454 | 0.1925 |

[a]Gene frequency.
[b]Standard error.

TABLE 2

Estimated gene frequencies for HLA-B antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |
| B7 | 12.1782 | 0.0445 | 10.5960 | 0.1024 | 4.2691 | 0.0827 | 6.4477 | 0.0918 | 10.9845 | 0.2432 |
| B8 | 9.4077 | 0.0397 | 3.8315 | 0.0634 | 1.3322 | 0.0467 | 3.8225 | 0.0715 | 8.5789 | 0.2176 |
| B13 | 2.3061 | 0.0203 | 0.8103 | 0.0295 | 4.9222 | 0.0886 | 1.2699 | 0.0416 | 1.7495 | 0.1013 |
| B14 | 4.3481 | 0.0277 | 3.0331 | 0.0566 | 0.5004 | 0.0287 | 5.4166 | 0.0846 | 2.9823 | 0.1316 |
| B18 | 4.7980 | 0.0290 | 3.2057 | 0.0582 | 1.1246 | 0.0429 | 4.2349 | 0.0752 | 3.3422 | 0.1391 |
| B27 | 4.3831 | 0.0278 | 1.2918 | 0.0372 | 2.2355 | 0.0603 | 2.3724 | 0.0567 | 5.1970 | 0.1721 |
| B35 | 9.6614 | 0.0402 | 8.5172 | 0.0927 | 8.1203 | 0.1122 | 14.6516 | 0.1329 | 10.1198 | 0.2345 |
| B37 | 1.4032 | 0.0159 | 0.5916 | 0.0252 | 1.2327 | 0.0449 | 0.7807 | 0.0327 | 0.9755 | 0.0759 |
| B41 | 0.9211 | 0.0129 | 0.8183 | 0.0296 | 0.1303 | 0.0147 | 1.2818 | 0.0418 | 0.4766 | 0.0531 |
| B42 | 0.0608 | 0.0033 | 5.6991 | 0.0768 | 0.0841 | 0.0118 | 0.5866 | 0.0284 | 0.2856 | 0.0411 |
| B46 | 0.0099 | 0.0013 | 0.0151 | 0.0040 | 4.9292 | 0.0886 | 0.0234 | 0.0057 | 0.0238 | 0.0119 |
| B47 | 0.2069 | 0.0061 | 0.1305 | 0.0119 | 0.0956 | 0.0126 | 0.1832 | 0.0159 | 0.2139 | 0.0356 |
| B48 | 0.0865 | 0.0040 | 0.1316 | 0.0119 | 2.0276 | 0.0575 | 1.5915 | 0.0466 | 1.0267 | 0.0778 |
| B53 | 0.4620 | 0.0092 | 10.9529 | 0.1039 | 0.4315 | 0.0266 | 1.6982 | 0.0481 | 1.0804 | 0.0798 |
| B59 | 0.0020 | 0.0006 | 0.0032 | 0.0019 | 0.4277 | 0.0265 | 0.0055 | 0.0028 | 0[c] | — |
| B67 | 0.0040 | 0.0009 | 0.0086 | 0.0030 | 0.2276 | 0.0194 | 0.0055 | 0.0028 | 0.0059 | 0.0059 |
| B70 | 0.3270 | 0.0077 | 7.3571 | 0.0866 | 0.8901 | 0.0382 | 1.9266 | 0.0512 | 0.6901 | 0.0639 |
| B73 | 0.0108 | 0.0014 | 0.0032 | 0.0019 | 0.0132 | 0.0047 | 0.0261 | 0.0060 | 0[c] | — |
| B51 | 5.4215 | 0.0307 | 2.5980 | 0.0525 | 7.4751 | 0.1080 | 6.8147 | 0.0943 | 6.9077 | 0.1968 |
| B52 | 0.9658 | 0.0132 | 1.3712 | 0.0383 | 3.5121 | 0.0752 | 2.2447 | 0.0552 | 0.6960 | 0.0641 |
| B5 unsplit | 0.1565 | 0.0053 | 0.1522 | 0.0128 | 0.1288 | 0.0146 | 0.1546 | 0.0146 | 0.1307 | 0.0278 |
| B5 total | 6.5438 | 0.0435 | 4.1214 | 0.0747 | 11.1160 | 0.1504 | 9.2141 | 0.1324 | 7.7344 | 0.2784 |
| B44 | 13.4838 | 0.0465 | 7.0137 | 0.0847 | 5.6807 | 0.0948 | 9.9253 | 0.1121 | 11.8024 | 0.2511 |
| B45 | 0.5771 | 0.0102 | 4.8069 | 0.0708 | 0.1816 | 0.0173 | 1.8812 | 0.0506 | 0.7603 | 0.0670 |
| B12 unsplit | 0.0788 | 0.0038 | 0.0280 | 0.0055 | 0.0049 | 0.0029 | 0.0193 | 0.0051 | 0.0654 | 0.0197 |
| B12 total | 14.1440 | 0.0474 | 11.8486 | 0.1072 | 5.8673 | 0.0963 | 11.8258 | 0.1210 | 12.6281 | 0.2584 |
| B62 | 5.9117 | 0.0320 | 1.5267 | 0.0404 | 9.2249 | 0.1190 | 4.1825 | 0.0747 | 6.9421 | 0.1973 |
| B63 | 0.4302 | 0.0088 | 1.8865 | 0.0448 | 0.4438 | 0.0270 | 0.8083 | 0.0333 | 0.3738 | 0.0471 |
| B75 | 0.0104 | 0.0014 | 0.0226 | 0.0049 | 1.9673 | 0.0566 | 0.1101 | 0.0123 | 0.0356 | 0.0145 |
| B76 | 0.0026 | 0.0007 | 0.0065 | 0.0026 | 0.0874 | 0.0120 | 0.0055 | 0.0028 | 0 | — |
| B77 | 0.0057 | 0.0010 | 0.0119 | 0.0036 | 0.0577 | 0.0098 | 0.0083 | 0.0034 | 0[c] | 0.0059 |
| B15 unsplit | 0.1305 | 0.0049 | 0.0691 | 0.0086 | 0.4301 | 0.0266 | 0.1820 | 0.0158 | 0.0059 | 0.0206 |
| B15 total | 6.4910 | 0.0334 | 3.5232 | 0.0608 | 12.2112 | 0.1344 | 5.2967 | 0.0835 | 0.0715 7.4290 | 0.2035 |
| B38 | 2.4413 | 0.0209 | 0.3323 | 0.0189 | 3.2818 | 0.0728 | 1.9652 | 0.0517 | 1.1017 | 0.0806 |
| B39 | 1.9614 | 0.0188 | 1.2893 | 0.0371 | 2.0352 | 0.0576 | 6.3040 | 0.0909 | 4.5527 | 0.1615 |
| B16 unsplit | 0.0638 | 0.0034 | 0.0237 | 0.0051 | 0.0644 | 0.0103 | 0.1226 | 0.0130 | 0.0593 | 0.0188 |
| B16 total | 4.4667 | 0.0280 | 1.6453 | 0.0419 | 5.3814 | 0.0921 | 8.3917 | 0.1036 | 5.7137 | 0.1797 |
| B57 | 3.5955 | 0.0252 | 5.6746 | 0.0766 | 2.5782 | 0.0647 | 2.1800 | 0.0544 | 2.7265 | 0.1260 |
| B58 | 0.7152 | 0.0114 | 5.9546 | 0.0784 | 4.0189 | 0.0803 | 1.2481 | 0.0413 | 0.9398 | 0.0745 |
| B17 unsplit | 0.2845 | 0.0072 | 0.3248 | 0.0187 | 0.3751 | 0.0248 | 0.1446 | 0.0141 | 0.2674 | 0.0398 |
| B17 total | 4.5952 | 0.0284 | 11.9540 | 0.1076 | 6.9722 | 0.1041 | 3.5727 | 0.0691 | 3.9338 | 0.1503 |
| B49 | 1.6452 | 0.0172 | 2.6286 | 0.0528 | 0.2440 | 0.0200 | 2.3353 | 0.0562 | 1.5462 | 0.0953 |
| B50 | 1.0580 | 0.0138 | 0.8636 | 0.0304 | 0.4421 | 0.0270 | 1.8883 | 0.0507 | 0.7862 | 0.0681 |
| B21 unsplit | 0.0702 | 0.0036 | 0.0270 | 0.0054 | 0.0132 | 0.0047 | 0.0771 | 0.0103 | 0.0356 | 0.0145 |
| B21 total | 2.7733 | 0.0222 | 3.5192 | 0.0608 | 0.6993 | 0.0339 | 4.3007 | 0.0755 | 2.3680 | 0.1174 |
| B54 | 0.0124 | 0.0015 | 0.0183 | 0.0044 | 2.6873 | 0.0660 | 0.0289 | 0.0063 | 0.0534 | 0.0178 |
| B55 | 1.9046 | 0.0185 | 0.4895 | 0.0229 | 2.2444 | 0.0604 | 0.9515 | 0.0361 | 1.4054 | 0.0909 |
| B56 | 0.5527 | 0.0100 | 0.2686 | 0.0170 | 0.8260 | 0.0368 | 0.3596 | 0.0222 | 0.3387 | 0.0448 |
| B22 unsplit | 0.1682 | 0.0055 | 0.0496 | 0.0073 | 0.2730 | 0.0212 | 0.0372 | 0.0071 | 0.1246 | 0.0272 |
| B22 total | 2.0852 | 0.0217 | 0.8261 | 0.0297 | 6.0307 | 0.0971 | 1.3771 | 0.0433 | 1.9221 | 0.1060 |
| B60 | 5.2222 | 0.0302 | 1.5299 | 0.0404 | 8.3254 | 0.1135 | 2.2538 | 0.0553 | 5.7218 | 0.1801 |
| B61 | 1.1916 | 0.0147 | 0.4709 | 0.0225 | 6.2072 | 0.0989 | 4.6691 | 0.0788 | 2.6023 | 0.1231 |

TABLE 2-continued

Estimated gene frequencies for HLA-B antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |
| B40 unsplit | 0.2696 | 0.0070 | 0.0388 | 0.0065 | 0.3205 | 0.0230 | 0.2473 | 0.0184 | 0.2271 | 0.0367 |
| B40 total | 6.6834 | 0.0338 | 2.0396 | 0.0465 | 14.8531 | 0.1462 | 7.1702 | 0.0963 | 8.5512 | 0.2168 |
| BX | 1.0922 | 0.0252 | 3.5258 | 0.0802 | 3.8749 | 0.0988 | 2.5266 | 0.0807 | 1.9867 | 0.1634 |

[a]Gene frequency.
[b]Standard error.
[c]The observed gene count was zero.

TABLE 3

Estimated gene frequencies of HLA-DR antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |
| DR1 | 10.2279 | 0.0413 | 6.8200 | 0.0832 | 3.4628 | 0.0747 | 7.9859 | 0.1013 | 8.2512 | 0.2139 |
| DR2 | 15.2408 | 0.0491 | 16.2373 | 0.1222 | 18.6162 | 0.1608 | 11.2389 | 0.1182 | 15.3932 | 0.2818 |
| DR3 | 10.8708 | 0.0424 | 13.3080 | 0.1124 | 4.7223 | 0.0867 | 7.8998 | 0.1008 | 10.2549 | 0.2361 |
| DR4 | 16.7589 | 0.0511 | 5.7084 | 0.0765 | 15.4623 | 0.1490 | 20.5373 | 0.1520 | 19.8264 | 0.3123 |
| DR6 | 14.3937 | 0.0479 | 18.6117 | 0.1291 | 13.4471 | 0.1404 | 17.0265 | 0.1411 | 14.8021 | 0.2772 |
| DR7 | 13.2807 | 0.0463 | 10.1317 | 0.0997 | 6.9270 | 0.1040 | 10.6726 | 0.1155 | 10.4219 | 0.2378 |
| DR8 | 2.8820 | 0.0227 | 6.2673 | 0.0800 | 6.5413 | 0.1013 | 9.7731 | 0.1110 | 6.0059 | 0.1844 |
| DR9 | 1.0616 | 0.0139 | 2.9646 | 0.0559 | 9.7527 | 0.1218 | 1.0712 | 0.0383 | 2.8662 | 0.1291 |
| DR10 | 1.4790 | 0.0163 | 2.0397 | 0.0465 | 2.2304 | 0.0602 | 1.8044 | 0.0495 | 1.0896 | 0.0801 |
| DR11 | 9.3180 | 0.0396 | 10.6151 | 0.1018 | 4.7375 | 0.0869 | 7.0411 | 0.0955 | 5.3152 | 0.1740 |
| DR12 | 1.9070 | 0.0185 | 4.1152 | 0.0655 | 10.1365 | 0.1239 | 1.7244 | 0.0484 | 2.0132 | 0.1086 |
| DR5 unsplit | 1.2199 | 0.0149 | 2.2957 | 0.0493 | 1.4118 | 0.0480 | 1.8225 | 0.0498 | 1.6769 | 0.0992 |
| DR5 total | 12.4449 | 0.0045 | 17.0260 | 0.1243 | 16.2858 | 0.1516 | 10.5880 | 0.1148 | 9.0052 | 0.2218 |
| DRX | 1.3598 | 0.0342 | 0.8853 | 0.0760 | 2.5521 | 0.1089 | 1.4023 | 0.0930 | 2.0834 | 0.2037 |

[a]Gene frequency.
[b]Standard error.

Tables 1, 2, and 3 derived from HLA Gene and Haplotype Frequencies in the North American Population: TheNational Marrow Donor Program Donor Registry, Mori, M. et al.

Determining Whether a Fragment with MHC Affinity is a Useful Epitope

As discussed above, a preliminary step of the disclosed method is to select from among the original population of peptide fragments a subpopulation of peptides with an actual or predicted MHC affinity. The selected fragments are analyzed further to determine which can be produced by a cell under in vivo conditions that could result in binding of the peptide to the selected MHC allele. All peptides that meet both criteria of MHC affinity and correct proteolytic processing are designated as "discovered epitopes." A variety of methods are available for determining which peptide fragments can be produced by proteolytic processing in vivo. These methods include elution of peptides from solubilized MHC and intact cells, computer sequence analysis of the proteolytic cleavage motifs, and in vitro analysis of actual peptide fragments produced by cellular proteolytic machinery.

In a preferred embodiment, a series of synthetic peptides centrally containing either individual or clustered candidate peptide sequences can be generated. Such peptides typically range in length from about 10 to about 75 amino acids. In a preferred embodiment, the synthetic peptide is between about 20 and 60 amino acids in length. In a more preferred embodiment, the cluster is between about 30 and 40 amino acids in length. Using standard peptide synthesis chemistry, including t-Boc protection chemistry, Fmoc protection chemistry, and the like, one of ordinary skill in the art can produce a population of candidate peptides for subsequent screening.

Alternatively, peptide fragments containing candidate peptides can be generated in vitro through protease digestion or chemical cleavage of the TAA or fragments thereof. Protease digestion to prepare such fragments of TAAs can employ a wide variety of known proteases, including but not limited to proteasome proteases, trypsin, α-chymotrypsin, bromelain, clostripain, elastase, endoproteinases, exoproteinases, proteinase K, ficin, papain, pepsin, plasmin, thermolysin, thrombin, trypsin, cathepsins, and others. Chemical methods can also be used to generate peptide candidates. Suitable chemicals or chemical reactions for cleaving peptide bonds include mild acid cleavage, cyanogen bromide, hydroxylamine, iodosobenzoic acid, 2-Nitro-5-thiocyanobenzoate, and the like. In one embodiment, the unfragmented TAA can be used, although the use of a particularly large initial sequence can complicate the analysis.

Regardless of how the fragments containing candidate peptides are created, determining which epitopes are produced by the cellular machinery is important. In one embodiment of the invention, proteasome digestion is used to estimate cellular epitope generation. In this embodiment, immune and housekeeping proteasomes are purified for in vitro use in order to assess the antigenic repertoire generated naturally from the two kinds of proteasomes. Differences between immune proteasomes and housekeeping proteasomes, the epitope products of these proteasomes, and the implications of these differences for vaccine design, are discussed in detail in copending U.S. patent application Ser. No. 09/560,465, entitled "EPITOPE SYNCHRONIZATION IN ANTIGEN PRESENTING CELLS," filed on even date herewith, which is incorporated herein by reference in its entirety.

Epitopes presented by class I MHC on the surface of either pAPCs or peripheral cells are produced by digestion of proteins within those cells by proteasomes. While it has been reported that the proteasomes of pAPCs are not identical to the proteasomes of peripheral cells, the significance of this difference has been heretofore unappreciated. This invention is based on the fact that when pAPCs and peripheral cells process a given TAA, the proteasomes active in the pAPCs generate epitope fragments that are different from the epitope fragments generated by the proteasomes that are active in the peripheral cells. For convenience of reference, and as defined above, the proteasomes that are predominantly active in pAPCs are referred to herein as "immune proteasomes" while the proteasomes that are normally active in peripheral cells are referred to wherein as "housekeeping proteasomes."

The significance of the differential processing of TAAs by pAPCs and peripheral cells cannot be overstated. This differential processing provides a unified explanation for why certain target cells are reluctant to recognition and attack by the immune system. Although pAPCs can take-up TAAs shed from target cells or presented on their surface, the pAPCs will consequently stimulate the production of CTLs to recognize an "immune epitope" (the epitope resulting from processing of the TAA by the immune proteasome), whereas the target cells display "housekeeping epitopes" (distinct fragments of the TAA generated by the housekeeping proteasome). As a consequence, the CTL response under physiological conditions is misdirected away from epitopes on the target cells.

Since CTL responses are induced by pAPCs by definition they target immune epitopes rather than house ing epitopes and thus fail to recognize target cells, which are therefore able to persist in the body. This fundamental "epitope compartmentalization" of the cellular immune response is the reason that some neoplastic cells can persist to form tumors; it is also the reason that some viruses and intercellular parasites can chronically infect cells without being eradicated by the immune system. With regard to infectious agents, normally thy cause the expression of immune proteasomes in the cells they infect. This results in the production of epitopes on the cell surface that are identical to those being presented by pAPCs to the immune system. Infection thus results in "epitope synchronization" between the immune system and the infected cell, subsequent destruction of the infected cells, and clearance of infectious agent from the body. In the case of some infectious agents, notably those that are capable of establishing chronic infections, they have evolved a means of preventing expression of immune proteasomes in the cells they infect. The proteasome in these cells are maintained in a housekeeping mode, thereby preventing epitope synchronization and attack by CTL. There is substantial evidence that this is a common mechanism used by virtually all chronic infectious agents.

One way to overcome this failure on the part of CTLs to recognize and eradicate certain target cells is to provide vaccines and treatment methods that are capable of "synchronizing"epitope presentation. Epitope synchronization in this context means that the pAPCs are made to present housekeeping epitopes, resulting in CTLs that can recognize the housekeeping epitopes displayed on target cells, and thereby attack and eliminate the target cells.

Generally, proteasomes are prepared by affinity purification from cell extracts. In a preferred embodiment, a cell lysate is prepared using standard techniques. The lysate is cleared by ultracentrifugation if erythrocytes are not the original source material. The prepared cell lysate is then purified from other cellular components using any one of a number of purification techniques including various forms of chromatography.

In one embodiment affinity chromatography is used to purify the proteasomes. The cell lysate is applied to an affinity column containing a monoclonal antibody (mAb) against one of the proteasomal subunits. The column is then washed to purify the bound proteasomes from other cellular material. Following washing, the bound proteasomes are then eluted from the column. The eluate is characterized in terms of protein content and proteolytic activity on a standard substrate.

Cleavage analysis using both housekeeping and immune proteasomes yields class I epitopes from various TAA. The epitopes that are presented by pAPCs correspond to cleavage products of the immune proteasome, while the epitopes presented by tumors and by many cells chronically infected with intracellular parasites correspond to cleavage products of the housekeeping proteasome. Once the digest is performed, the particular molecular species produced are identified. In a preferred embodiment, this is accomplished by mass spectrometry. This allows the rapid identification of natural peptide fragments that are produced by either of the two kinds of proteasomes. In another embodiment, cleavage of the target antigen or fragments thereof by immune and housekeeping proteasomes, or by endosomal/lysosomal proteases (see below), is predicted by computer modeling based on cleavage motifs of the relevant proteolytic activities.

Whereas class I MHC is loaded primarily with proteasomally derived peptides as it initially folds in the endoplasmic reticulum, the binding cleft of class II MHC is blocked by the so-called invariant chain (Ii) in this compartment. Loading of peptide for class II MHC takes place primarily in the endosomal compartment, utilizing peptides generated by endosomal and lysosomal proteases. Thus if in vitro identification of MHC class II epitopes is desired, preparations of proteases from endosomal and/or lysosomal fractions can be substituted for the proteasomes. A variety of methods to accomplish this substitution are described in the literature. For example, Kido & Ohshita, Anal. Biochem., 230:41–7 (1995); Yamada, et al., J. Biochem. (Tokyo), 95:1155–60 (1984); Kawashima, et al., Kidney Int., 54:275–8 (1998); Nakabayshi & Ikezawa, Biochem. Int. 16:1119–25 (1988); Kanaseki & Ohkuma, J. Biochem. (Tokyo), 110:541–7 (1991); Wattiaux, et al., J. Cell Biol., 78:349–68 (1978); Lisman, et al., Biochem. J. 178:79–87 (1979); Dean, B., Arch. Biochem. Biophys., 227:154–63 (1983); Overdijk, et al., Adv. Exp. Med. Biol., 101:601–10 (1978); Stromhaug, et al., Biochem. J., Biochem. J., 335:217–24 (1998); Escola, et al., J. Biol. Chem. 271:27360–5 (1996); Hammond, et al., Am. J. Physiol., 267:F516–27 (1994); Williams & Smith, Arch. Biochem. Biophys. 305:298–306 (1993); Marsh, M., Methods Cell Biol., 31:319–34 (1989); and Schmid & and Mellman, Prog. Clin. Biol. Res., 270:35–49 (1988) all disclose methods to prepare suitable proteolytic preparations. Each of the foregoing references is hereby incorporated by reference in its entirety.

In another embodiment, the digestion to determine which epitopes the cellular machinery produces, takes place within a cell expressing the TAA or a fragment thereof. For class I epitopes it is preferred that the type of proteasome expressed by the cell be determined, for example, by western blotting. The MHC epitopes produced can then be eluted from either solubilized and purified MHC as described in Falk, K et al. Nature 351:290, 1991, or directly from the intact cell as described in U.S. Pat. No. 5,989,565, both of which references are incorporated herein by reference in their entirety. Eluted fragments are then identified by mass spectrometry.

Analysis of Target Protein Fragments

The molecular species detected by mass spectrometry are compared with the candidate peptides predicted above. For the case of class I epitopes, species that are as long as, or longer than, a candidate peptide and share its C-terminus are desired; N-terminal trimming of at least up to 25 amino acids can occur independently of the proteasome (Craiu, A. et al. Proc. Natl. Acad. Sci. USA 94:10850–55, 1997). Class II MHC is much less limited in terms of the length of the peptides it will bind, so the absence of cleavage in the middle of the epitope becomes the primary criterion, rather than generation of a correct end.

A selected digestion product is then synthesized and used as a standard in an analytic method such as HPLC versus an aliquot of the digest. This provides a further check on the identity of the digestion product and allows its yield to be determined. In rare cases more than one potential product may have similar enough masses and chemical characteristics that they may not be reliably differentiated by these methods. In such cases the HPLC peak can be collected and subjected to direct sequencing to confirm identity.

Analysis of Peptides for MHC Binding

The epitope is synthesized and tested for its ability to bind a MHC receptor. For example, in one preferred assay, cells displaying the MHC I receptor can be used to measure the binding affinity of candidate peptides labeled with a radionuclide. Another preferred approach measures the ability of a peptide to bind to an MHC I receptor using a cell culture-based assay. In this assay, cells lacking transporters associated with antigen processing (TAP) are used to determine whether or not a candidate peptide has the ability to bind to the MHC I receptor. TAP cells have the phenotype in which class 1 MHC proteins do not always fold properly, and surface expression of MHC I is thus reduced or abolished. When the cell is flooded with exogenous peptide that can bind to the MHC I cleft, expression of the receptor is restored. This can be monitored by several means such as RIA, FACS, and the like. Using TAP⁻ cells, one of skill in the art can screen large numbers of potential candidate peptides for receptor binding without having to perform detailed binding affinity analysis.

The analysis methods of the various embodiments of the invention are useful in examining candidate peptides generated in a variety of ways. For example, the described analysis can be used in evaluating multiple candidate peptides generated through in vitro methods or by computational analysis, to identify those candidate sequences that have MHC receptor binding characteristics. Preferred candidate peptides in this embodiment of the invention are those that are already known to be products of proteolytic production by housekeeping and/or immune proteasomes. Both in vivo cleavage products and in vitro cleavage products that are shown or predicted to bind to MHC are properly designated as "discovered epitopes."

Epitope synchronization technology and vaccines for use in connection with this invention are disclosed in copending U.S. patent application Ser. No. 09/560,465 entitled "EPITOPE SYNCHRONIZATION IN ANTIGEN PRESENTING CELLS," filed on even date herewith, which is incorporated herein by reference in its entirety ("As has been discussed herein, effective cellular immunity is based on synchronized epitope presentation between the pAPCs and the infected peripheral cells. In the absence of epitope synchronization, target cells are not recognized by T cells, even if those T cells are directed against TAAs. Cancer cells and cells harboring persistent intracellular parasites elude the cellular immune response because they avoid epitope synchronization. "natural" epitope synchronization involves activation of immune proteasomes in infected cells so that the infected cells display immune epitopes and are thus recognized by T cells induced by pAPCs. Yet cancers and cells infected by persistent intracellular parasites do not have active immune proteasomes and thus go unrecognized by the normal array of induced T cells. The vaccines and methods of preferred embodiments of the present invention thus represent, essentially, a "reverse" epitope synchronization, causing the pAPCs to display housekeeping epitopes to address situations in which target cells do not display immune epitopes . . . Certain embodiments also provide a second wave of epitope synchronization by inducing pAPCs to display both housekeeping epitopes and immune epitopes corresponding to a selected target cell. Thus, in these dual epitope embodiments, once the target cells are effectively attacked by T cells that recognize housekeeping epitopes, a switch by the target cells to immune proteasome processing does not result in a loss of immune recognition. This is because of the presence of the immune epitope in the vaccine, which acts to induce a population of T cells that recognize immune epitopes. Preferred embodiments of the present invention are directed to vaccines and methods for causing a PAPC or population of TAPCs to present housekeeping epitopes that correspond to the epitopes displayed on a particular target cell. In one embodiment, the housekeeping epitope is a TuAA epitope processed by the housekeeping proteasome of a particular tumor type. In another embodiment, the housekeeping epitope is a virus-associated epitope processed by the housekeeping proteasome of a cell infected with a virus. This facilitates a specific T cell response to the target cells. Concurrent expression by the pAPCs of multiple epitopes, corresponding to different induction states (pre- and post-attack), can drive a CTL response effective against target cells as they display either housekeeping epitopes or immune epitopes." "TILs isolated from patient biopsies, or PBMCs from blood of donors or patients can be used to identify housekeeping epitopes using methods that are commonly described in the published literature. To identify housekeeping epitopes, the target cells used to test for active killing by PBMCs or TILs are confirmed to express only the housekeeping proteasomes, and not to express at significant levels the immune proteasome. PBMCs from donor blood are stimulated in vitro using a panel of peptide antigens with predicted affinity for the class I HLA allele expressed on the blood cells being used. Each PBMC sample is stimulated with a specific class I peptide antigen for one week, preferably with the combination of cytokines such as IL-2 or IL-12 to enhance the activity of the T cells. This stimulation is repeated at least three times to induce clonal expansion of T cells specific against the peptide. A standard chromium release assay is performed using target cells that are known to express the protein containing the epitope and exclusively the housekeeping proteasome. Evidence of killing of the target cells as measured by chromium release indicates that the peptide used to stimulate the PBMCs is present as a housekeeping epitope on the surface of the target cell. Tumors expressing this protein are thus candidate targets for a vaccine containing the epitope.").

Epitope clusters for use in connection with this invention are disclosed in copending U.S. patent application Ser. No. 09/561,571 entitled "EPITOPE CLUSTERS," filed on even date herewith, which is incorporated herein by reference in its entirety. Nucleic acid constructs useful as vaccines in accordance with the present invention are disclosed in copending U.S. patent application Ser. No. 09/561,572 entitled "EXPRESSION VECTORS ENCODING EPITOPES OF TARGET-ASSOCIATED ANTIGENS," filed on even date herewith, which is incorporated herein by reference in its entirety.

The following examples are intended for illustration purposes only, and should not be construed as limiting the scope of the invention in any way.

EXAMPLES

Example 1

Purification of Proteasome Complexes

A. Proteasome Complexes from Blood Cells

Concentrated erythrocyte bags were obtained from a local blood bank, (HemaCare, Van Nuys, Calif.). The contents of each bag were poured into 200 ml centrifuge tubes and washed 3 times with PBS by centrifugation at 2000 RPM for 10 minutes at room temperature in a swinging bucket rotor of a Megafuge 2.0 (Heraeus, Southplainfield, N.J.). After the last wash the samples were pooled in one container, to minimize variability among tubes, and then re-divided into several centrifuge tubes. The cells were centrifuged again at 2000 RPM for 10 min. The residual PBS was aspirated. The pellet was stored at −70° C. until use.

B. Proteasome Complexes from Tumor Cells

Raji cells, a Burkitt's lymphoma cell line, were obtained from ATCC, (American Type Culture Collection, Manassas, Va.). The cells were grown using standard cell culture methods and stimulated with INF-Gamma (100–500 U/ml) (Pharmingen, San Diego, Calif.). Expression of immune proteasome subunits was confirmed separately by immunohistochemsitry on the culture, and SDS-PAGE on a sample of the cell lysate. The cells were collected by centrifugation, washed with PBS and stored at −70° C. until use.

C. Further Processing of Proteasome Complexes

Blood or lymphoma tumor cell pellets (frozen) were thawed in a 37° C. bath and ddH$_2$O was added to each tube. The cell suspension was homogenized in a 40 ml Dounce homogenizer. Further, for the tumor cells, the cell homogenate was centrifuged at 2000 rpm to remove cell debris. The supernatant was centrifuged at 10,000 rpm at 4° C. for 10 minutes and further centrifuged at 50,000 rpm at 4° C. for 30 minutes in a T-1270 rotor (Sorval, Newtown, Conn.).

The homogenates were passed through filter paper to remove debris, and then pooled together. A 68% sucrose solution was added to the pooled homogenate sample. An antibody-Sepharose preparation was incubated with the homogenate for three hours at room temperature in a rotator. The suspension was centrifuged and washed 3× with TBS and further thoroughly washed over vacuum funnel 6–8 X. Proteasomes were eluted in TBS (pH 7.6) and the optical density of the eluate was measured. The proteasome preparation was dialyzed overnight at 4° C. against 20 mM Tris (pH 7.6) using cellulose membrane MWCO 1000. The next day the proteasome preparation was concentrated by ultra-filtration in a Millipore ULTRAFREE-15 centrifugation device (Millipore, Danbury, Conn.). The proteasomes, at a concentration of 4 mg/ml, were then aliquotted and stored at −20° C. until use. The proteasomes were tested for activity and specificity by digestion of a fluorogenic substrate or a control peptide yielding known fragments. The following peptides are suitable for use as control peptides for immune proteasome assays: MLLAVLYCLLWSFQTS (SEQ ID NO: 63); HSYTTAEEAAGITILTVILGVL (SEQ ID NO: 64); EAASSSSTLVEVTLGEVPAAESPD (SEQ ID NO: 65); EFLWGPRALVETSYVKVLHH MVKI (SEQ ID NO: 66); APEEKIWEELSVLEVFEGR (SEQ ID NO: 67); and ELMEVDPIGH LYIFAT (SEQ ID NO: 68). Underlined residues indicate proteolytic cleavage sites. Peptide FLWG-PRALVETSYVK (SEQ ID NO: 69) is suitable as a control peptide for housekeeping proteasome assays.

D. Quantitation and Activity Analysis of Proteasome Preparations

An enzyme-linked immunosorbant assay (ELISA) was used to quantitate the proteasome preparations described above. ELISA techniques are well known in the art and are discussed generally in Ausubel, et al., "Short Protocols in Molecular Biology," 3rd Ed., Unit 11.2 (1997), which is hereby incorporated by reference in its entirety. Hybridoma cells (MCP-21) producing a monoclonal anti-human proteasome antibody were obtained from the European Collection of Cell Culture ((ECACC), UK) and were maintained using standard cell culture techniques and equipment. Hybridoma supplement (Gibco BRL, Rockville, Md.) was added to the antibody-producing cells.

Upon reaching cell density of 500,000 cells/ml in an approximate volume of 2–3 liters, the cells were removed by centrifugation and the supernatant was collected. Secretion of mAb in the medium was monitored periodically by optical density (O.D.) using a Lambda 20 Spetrophotometer (Perkin Elmer, Norwalk, Conn.).

The supernatant was passed over a protein G sepharose column (Amersham/Pharmacia Biotech Piscataway, N.J.). The column was washed with PBS and the antibody was eluted in a 0.1M glycine buffer, pH 2.2. The optical density of the eluate fractions was measured at 280 nm, and the positive factions were collected. The antibody was dialyzed against 2L of PBS for 2 days at 4° C. and stored until use.

The antibody was bound to CNBr-activated Sepharose 4B (Amersham Pharmacia biotech, Piscataway, N.Y.). The antibody-Sepharose complex was washed alternately 5–7 times with 0.1M sodium acetate saline, pH 4 and 0.1M sodium borate saline, pH 8 and finally suspended in Tris buffered saline (TBS), pH 8. The preparation was stored at 4° C. until use.

E. Identification of Housekeeping and/or Immune Proteasomes by Western Blotting

Both of the following protocols start with a membrane onto which proteins extracted from cells of interest have been transferred after electrophoretic separation.

A. Chromogenic Protocol:

1. Wash the membrane for 5 min in 20 ml PBS-T (phosphate buffered saline, pH 7.4+0.1% Tween-20) at room temperature on an orbital shaker (RT/shaker).
PBS (Sigma, Cat. No. P-3813)
(Volumes may vary with type of container throughout).
2. Incubate the membrane for 5 min in 20 ml PBS-T, 3% H$_2$O$_2$ at RT/shaker;
2 ml 30% H$_2$O$_2$+18 ml PBS-T
3. Wash the membrane 3×5 min with PBS-T at RT/shaker.
4. Block overnight in 20 ml PBS-T/5% nonfat dry milk at 4° C./shaker:
20 ml PBS-T+1 g milk
5. Rinse the membrane in PBS-T.
6. incubate the membrane in 5 ml of primary antibody (Affinity Research Products Ltd, United Kingdom) in blocking buffer for 2 hrs at RT/shaker.

| α-LMP 2 antiserum (mouse) (Cat. No. PW 8205) | 1:5000 |
| α-LMP 2 antiserum (human) (Cat. No. PW 8345) | 1:10000 |
| α-LMP 7 antiserum (Cat. No. PW 8200) | 1:20000 |

These conditions are for the preceding antibodies only. Conditions for every antibody must be determined empirically.

7. Wash the membrane as in step 3
8. Incubate the membrane in 5 ml of secondary antibody (Vector Laboratories, Inc., Burlingame, Calif.) in blocking buffer for 30 min at RT/shaker.
   GARB (Goat anti Rabbit) (for antisera) (Vector Labs Cat. No. BA-1000)1:2000
   Horse anti mouse (for monoclonal antibodies) (Vector Labs Cat. No, BA-2000) 1:1000
9. Wash the membrane as in step 3.
10. Incubate the membrane in 5 ml of ABC (Vector Laboratories, Cat. No. PK-6100) in PBS-T for 30 min:
    Make ABC at least 30 min before using as follows:
    A=5 ul/1 ml=25 ul/5 ml
    B=5 ul/1 ml=25 ul/5 ml
    5 ul A+5 ul B>mix>let stand at 4 C>add 990 ul PES-T
    Dilute ABC in PBS-T just before using
11. Wash the membrane as in step 3.
12. Detection:
    1) transfer 5 ml of 0.2 M PB into a $1^{st}$ 15 ml tube
       0.4M Phosphate buffer:
       90.4 ml of Sodium Phosphate Monobasic (1M)
       619.2 ml of Sodium Phosphate Dibasic (0.5M)
       pH to 7.4
       QS to 1L
    2) transfer 2.8 ml of 0.2M PB into a $2^{nd}$ 15 ml tube
    3) transfer 2 ml of 1% Glucose into a $3^{rd}$ 15 ml tube
    4) weigh 6 mg of ANS (Ammonium Nickel Sulfate) and transfer it into $1^{st}$ 15 ml tube; vortex
    5) add 110 µl of Glucose Oxidase (Sigma, Cat. No. G-6891) into an eppendorf tube
    6) add 110 µl of DAB substrate (Daiminobenzidine HCl, KPL, Maryland Cat. No. 71-00-46) into another eppendorf tube
    7) Mix in the hood: 5 ml PB+2 ml Glucose+110 µl GO+110 µl DAB+2.8 ml 0.2M PB
13. Apply detection mixture on the membrane and set up timer. Record length of incubation in chromogen.
14. After bands became visible enough wash the membrane 3 times with 0.2M PB.
15. Shake in PBS overnight at RT.

B. Chemiluminescence Protocol:
1. Rinse the membrane twice in TBS-T (Tris-buffered saline pH7.6+0.1% Tween-20). Tris-buffered saline:
   2.42 g Tris base (20 mM)
   8 g sodium chloride (137 mM)
   3.8 ml 1M hydrochloric acid
2. Block overnight in 20 ml of blocking buffer (TBS-T/ 5% nonfat dry milk)
   4° C./shaker:
   20 ml TBS-T+1 g milk
   Volumes depend on typo of container
3. Rinse the membrane twice with TBS-T.
4. Incubate the membrane in 5 ml of primary antibody (Affinity Research Products Ltd. United Kingdom) in blocking buffer for 2 hrs at RT/shaker:

| α-LMP 2 antiserum (mouse) (Cat. No. PW 8205) | 1:5000 |
| α-LMP 2 antiserum (human) (Cat. No. PW 8345) | 1:10000 |
| α-LMP 7 antiserum (Cat. No. PW 8200) | 1:20000 |
| α-20S proteasome α2 subunit monoclonal antibody (Cat. No. PW 8105) | 1:1000 |

5. Wash the membrane in 20 ml of TBS-T at RT/shaker. Briefly rinse the membrane using two changes of TBS-T then wash once for 15 minutes and twice for 5 minutes with fresh changes of the washing buffer at room temperature.
6. Incubate the membrane in 5 ml of HRP labeled (Horseradish peroxidase-labeled) secondary antibody (Amersham; Cat# NIF 824 or NIF 825) 1:1000 dilution in blocking buffer for 1 h at RT/shaker
7. Wash the membrane as in step 5.
8. Mix an equal volume of detection solution 1 (Amersham, Cat#RPN2109) and detection solution 2 (Amersham, Cat#RPN2109) (1 ml+1 ml).
9. Drain the excess buffer from the washed membrane and put it on a piece of Saran Wrap, protein side up. Add the detection reagent to cover the membrane.
10. Incubate for 1 minute at room temperature without agitation.
11. Drain off excess of detection reagent and transfer the membrane to Kodak Digital Science Image Station 440CF protein side down. Develop and quantify the signal according to the manufacturer' instructions.

The presence of housekeeping-specific subunits (in either protocol) is directly assessed using:

| α-β1 (Y) subunit monoclonal antibody (Cat. No. PW 8140) | 1:1000 |
| α-β2 (Z) subunit monoclonal antibody (Cat. No. PW 8145) | 1:1000 |

(Affinity Research Products Ltd, United Kingdom).

Example 2

Generation of Predicted MHC 1 Peptide Cleft Binding Peptides Using Algorithmic Modeling A population of candidate MHC I binding peptides, generated from the amino acid sequence of human carcinoembryonic antigen precursor (CEA) (GENBANK ACCESSION PO6731), was produced using an algorithm. The particular algorithm is available at <<http://134.2.96.221/ scripts/hlaserver.dll/EpPredict.htm>>, as discussed above and hereby incorporated by reference in its entirety. Once the algorithm was accessed, the amino acid sequence for CEA was provided. Next, parameters for the length of the epitope (decamers) and the particular MHC allele (H2-Db) of interest were selected. Following this, the data were submitted for algorithmic analysis. The resulting data are shown in Table II.

TABLE II

Fragments of CEA having Predicted Affinity for H2-Db

| POS | 1 | 2 | 3 | 4 | 5 | 6 | 7 | 8 | 9 | 0 | Score | Seq Id no |
|---|---|---|---|---|---|---|---|---|---|---|---|---|
| 547 | L | Q | L | S | N | G | N | R | T | L | 26 | 1 |
| 369 | L | Q | L | S | N | D | N | R | T | L | 26 | 2 |
| 191 | L | Q | L | S | N | G | N | R | T | L | 26 | 3 |

TABLE II-continued

Fragments of CEA having Predicted Affinity for H2-Db

| POS | 1 | 2 | 3 | 4 | 5 | 6 | 7 | 8 | 9 | 0 | Score | Seq Id no |
|---|---|---|---|---|---|---|---|---|---|---|---|---|
| 53  | L | L | V | H | N | L | P | Q | H | L | 26 | 4 |
| 371 | L | S | N | D | N | R | T | L | T | L | 25 | 5 |
| 549 | L | S | N | G | N | R | T | L | T | L | 24 | 6 |
| 193 | L | S | N | G | N | R | T | L | T | L | 24 | 7 |
| 299 | C | Q | A | H | N | S | D | T | G | L | 23 | 8 |
| 100 | I | I | Y | P | N | A | S | L | L | I | 21 | 9 |
| 578 | S | A | N | R | S | D | P | V | T | L | 19 | 10 |
| 576 | S | V | S | A | N | R | S | D | P | V | 19 | 11 |
| 504 | S | I | S | S | N | N | S | K | P | V | 18 | 12 |
| 356 | W | W | V | N | N | Q | S | L | P | V | 18 | 13 |
| 178 | W | W | V | N | N | Q | S | L | P | V | 18 | 14 |
| 148 | S | I | S | S | N | N | S | K | P | V | 18 | 15 |
| 127 | S | D | L | V | N | E | E | A | T | G | 18 | 16 |
| 645 | I | T | P | N | N | N | G | T | Y | A | 17 | 17 |
| 540 | S | L | P | V | S | P | R | L | Q | L | 17 | 18 |
| 362 | S | L | P | V | S | P | R | L | Q | L | 17 | 19 |
| 326 | F | I | T | S | N | N | S | N | P | V | 17 | 20 |
| 250 | R | S | G | E | N | L | N | L | S | C | 17 | 21 |
| 184 | S | L | P | V | S | P | R | L | Q | L | 17 | 22 |
| 140 | V | Y | P | E | L | P | K | P | S | I | 17 | 23 |
| 40  | S | T | P | F | N | V | A | E | G | K | 17 | 24 |
| 29  | N | P | P | T | T | A | K | L | T | I | 17 | 25 |
| 655 | C | F | V | S | N | L | A | T | G | R | 16 | 26 |
| 608 | G | A | N | L | N | L | S | C | H | S | 16 | 27 |
| 606 | L | S | G | A | N | L | N | L | S | C | 16 | 28 |
| 604 | S | Y | L | S | G | A | N | L | N | L | 16 | 29 |
| 571 | C | G | I | Q | N | S | V | S | A | N | 16 | 30 |
| 496 | V | S | A | E | L | P | K | P | S | I | 16 | 31 |
| 465 | S | N | I | T | E | K | N | S | G | L | 16 | 32 |
| 453 | G | N | I | Q | Q | H | T | Q | E | L | 16 | 33 |
| 441 | S | N | P | P | A | Q | Y | S | W | L | 16 | 34 |
| 393 | C | G | I | Q | N | E | L | S | V | D | 16 | 35 |
| 242 | I | S | P | L | N | T | S | Y | R | S | 16 | 36 |
| 91  | P | G | P | A | Y | S | G | R | E | I | 16 | 37 |
| 43  | F | N | V | A | E | G | K | E | V | L | 16 | 38 |
| 693 | I | G | V | L | V | G | V | A | L | I | 15 | 39 |
| 684 | S | A | G | A | T | V | G | I | M | I | 15 | 40 |
| 510 | S | K | P | V | E | D | K | D | A | V | 15 | 41 |
| 482 | S | A | S | G | H | S | R | T | T | V | 15 | 42 |
| 428 | R | P | G | V | N | L | S | L | S | C | 15 | 43 |
| 399 | L | S | V | D | H | S | D | P | V | I | 15 | 44 |
| 372 | S | N | D | N | R | T | L | T | L | L | 15 | 45 |
| 332 | S | N | P | V | E | D | E | D | A | V | 15 | 46 |
| 329 | S | N | N | S | N | P | V | E | D | E | 15 | 47 |
| 307 | G | L | N | R | T | T | V | T | T | I | 15 | 48 |
| 289 | I | T | V | N | N | S | G | S | Y | T | 15 | 49 |
| 280 | S | T | Q | E | L | F | I | P | N | I | 15 | 50 |
| 277 | F | Q | Q | S | T | Q | E | L | F | I | 15 | 51 |
| 222 | S | A | R | R | S | D | S | V | I | L | 15 | 52 |
| 221 | V | S | A | R | R | S | D | S | V | I | 15 | 53 |
| 154 | S | K | P | V | E | D | K | D | A | V | 15 | 54 |
| 135 | T | G | Q | F | R | V | Y | P | E | L | 15 | 55 |
| 49  | K | E | V | L | L | L | V | H | N | L | 15 | 56 |
| 34  | A | K | L | T | I | E | S | T | P | F | 15 | 57 |

The table above arbitrarily cuts off scores below 15. The algorithm can produce scores of less than 15.

Example 3

Digestion of Peptide Precursors Using Immune and Housekeeping Proteasomes to Determine Fragments Produced by Proteolytic Digestion Peptides were synthesized using a 433A ABI synthesizer. Peptides were produced in 0.25 mmole quantities using Fastmoc chemistry. The peptides were tested for solubility and once solubilized, a 2 mM solution was prepared and divided into 25–30 μL aliquots which were stored at −20° C. for future use. Timed digest reactions, typically consisting of 2 μl of peptide and 4 μl of proteasome, were conducted with t=0 as a control and an incubation of the peptide with water instead of the proteasome as a further control. The reaction was carried out at 37° C. and ended by the addition of 10% TFA (trifluroacetic acid) on dry ice. The frozen samples were then analyzed by MALDI-TOF mass spectroscopy (MS) as described in Example 4, below.

An optional desalting step can be performed on the digests prior to MS analysis using the ZIP-TIP method (Millipore, Boston, Mass.). The ZIP TIP is a specially designed pipet tip which contains a bed of spherical silica resin. The sample is bound to the tip, which is pre-equilibrated with 0.1% TFA, and then eluted with 50% Acetonitrile 0.1% TFA elution buffer.

Example 4

Identification and Quantitation of Relevant Proteolytic Fragments by HPLC and Mass Spectrometry A. Identifying Sequences of Therapeutic Interest The amino acid sequence of a protein of interest is entered into a computer, and the algorithm of Rammensee, et al., is used to generate 9- or 10-amino-acid-long sequences predicted to bind a particular HLA receptor. The algorithm also ranks these predicted epitopes according to how well they match the binding motif.

Synthetic peptides containing the sequence of the identified potential epitopes are then constructed to encompass the epitope candidate sequence and at least 3–5 residues proximal to its termini. The residues added to the ends of a particular epitope candidate are to ensure that the proteasome complex encounters a processing environment similar to that found within the cell, hence increasing the likelihood that it performs its proteolytic functions normally. Additional residues normally found proximal to the ends of the epitope candidate may be added if necessary to help increase the solubility of the peptides.

Peptides are synthesized on an Applied Biosystems 433A Peptide Synthesizer (Applied Biosystems, Norwalk, Conn.) using standard Fmoc solid phase synthesis methodologies. The synthesizer is equipped with a conductivity feedback monitoring system which allows for increased reaction times for sequences that contain stretches of difficult to deprotect and difficult to couple residues. After synthesis, the peptides are cleaved from their support with trifluoroacetic acid in the presence of appropriate scavengers, precipitated with ether and then lyophilized.

The crude peptides are then dissolved in a suitable solvent at 0.5 mg/ml. Five microliters (5 μl) of this solution is then analyzed on a Shimadzu analytical reverse phase HPLC system (Shimadzu Scientific Instruments, Columbia, Md.) using a 0.1% TFA water-acetonitrile gradient. Typically, a C-18 silica column (Machery-Nagel # 720051.40, (Machery-Nagel GmbH, Germany)) is used for hydrophillic and a phenyl silica column (Vydac # 219TP5415 (The Separations Group, Inc., Hesperia, Calif.)) is used for hydrophobic peptides. The gradients used vary from 0–40% acetonitrile for hydrophillic to 30–70% acetonitrile for hydrophobic peptides. The peptides are subsequently purified on a Varian Prostar HPLC system (Varian, Inc., Palo Alto, Calif.) using similar gradients and semi-preparative versions of the above-mentioned columns (Machery Nagel # 715802, and Vydac 219TP510). The major HPLC fractions from the first preparative injection of the peptide are analyzed using a MALDI-TOF mass spectrometer to identify the desired component. The corresponding peaks from subsequent injections are collected, pooled and lyophilized, and a sample is taken to verify retention time and chromatographic purity by analytical HPLC using the system described above. These purified peptides are then ready for digestion by the proteasome preparation.

B. Proteasome Assay

Immune or housekeeping proteasome complexes are isolated by the method of Levy, (Morel, S., et al., Immunity 12:107–117 (2000), and the references cited therein, which are all incorporated by reference in their entireties) described above. The purified peptide is dissolved in an appropriate buffer to a concentration of about 1 to 2 mM and added to approximately 2 volumes of the proteasome preparation. The buffer chosen must solvate the peptide without interfering with the digestion process. An additional digest is prepared using the positive control peptide described above to verify proper functioning of the proteasome preparation used. These are incubated at 37° C. for periods of up to 120 minutes and then the digestion is stopped by the addition of dilute trifluoroacetic acid; the samples are analyzed immediately by mass spectrometry, or they are frozen on dry ice until analysis. The digest reaction can also be halted by putting samples on ice for immediate analysis by mass spectrometry.

C. MALDI-TOF Mass Spectrometric Analysis of the Digest

Approximately 0.5 μl of each digest was mixed with an equal volume of the matrix solution (10 mg/ml dihydroxybenzoic acid in 70% EtOH, pH 2–3) directly on the sample slide and allowed to air dry at about 40° C. The samples were then analyzed on a Lasermat™ MALDI-TOF mass spectrometer (Thermo Bioanalysis, Santa Fe, N.Mex.) that was calibrated with suitable molecular weight standards.

The computer programs (either "Peptide" software, (Lighthouse Data), or "Dynamo" (ThermoBioanalysis Ltd., U.K.)) developed for the proteasome assay generates the sequence and molecular weight of all the possible fragments that satisfy both requirements of having the correct C-terminus of any predicted epitope, and of containing the full length of that epitope or longer.

Figure 2:
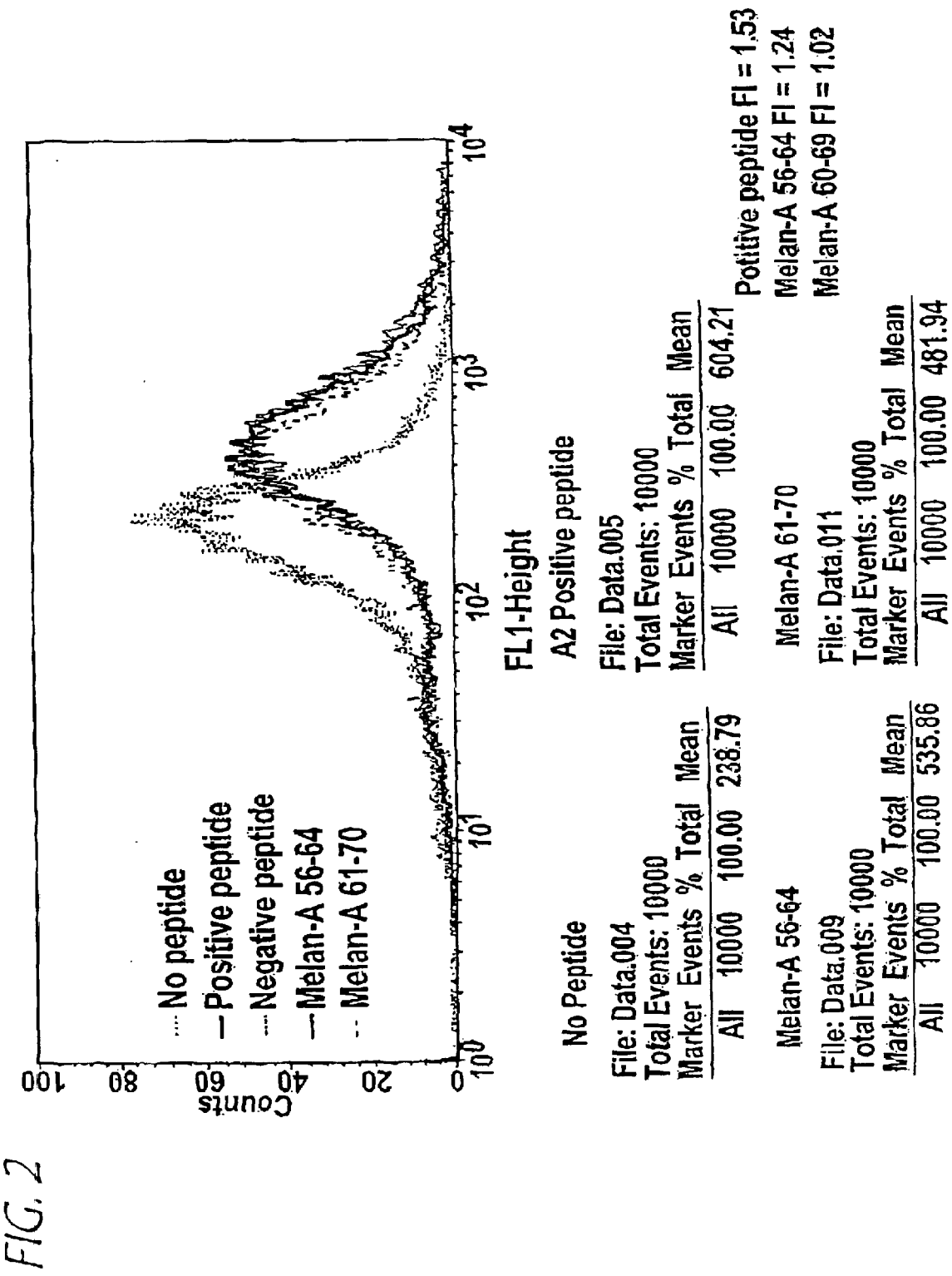
FIG. 2 depicts the results of a flow cytometry assay verifying HLA binding by Melan-A epitopes.

When the MALDI-TOF results showed that a particular molecular weight was represented in a digestion mixture, the corresponding peptide was synthesized, purified, identified by MALDI-TOF and then subjected to reverse phase analytical HPLC to establish a standard retention time and an approximate mass to peak area ratio. These procedures are directly analogous to those described above. A replicate proteasome digest was then diluted in an appropriate solvent and analyzed using the same analytical HPLC method. When the digest gives a peak in good yield that has the same retention time as that of the standard, it is almost certain that it is due to the presence of that sequence in the digest. When there is any ambiguity due to the possible generation of other fragments that would give rise to the same or similar mass spectrometry results, the suspect component can be collected and set aside for sequencing to confirm identity. The analytical HPLC also importantly provides relatively accurate quantitation of the peptide product in the digest, which allows determination of whether a given peptide is a minor or a major product of the digest, which indicates whether the epitope is efficiently produced by the proteasome. Using the above method, housekeeping epitopes were identified. FIG. 2 shows the results of a flow cytometry assay to verify HLA binding by these epitopes. This assay is discussed in Example 5.

Example 5

Determine the MHC Binding Ability of Selected Peptides

Binding of a candidate epitope to HLA-A2.1 was assayed according to the method of Stauss et al., (Proc Natl Acad Sci USA 89(17):7871–5 (1992)). T2 cells, which express empty or unstable MHC molecules on their surface, were washed twice and suspended at 5×10⁶ cells/ml in serum-free complete Iscove's modified Dulbecco's medium (IMDM). $\beta_2$ microglobulin (Sigma, St. Louis, Mo.) was added at 5 μg/ml and the cells distributed to a 96-well U-bottom plate at 5×10⁵ cells/well. Peptides were added at 100, 10, 1 and 0.1 μg/ml. The plate was rocked gently for 2 minutes and then incubated for 4 hours in a 5% $CO_2$ incubator at 37° C. After the unbound peptide was removed by washing twice with IMDM, a saturating amount of monoclonal antibody W6/32 (Sigma) was added. After incubation for 30 minutes at 4° C., cells were washed with PBS supplemented with 1% heat-inactivated FCS, 0.1%(w:v) sodium azide, pH 7.4–7.6 (staining buffer), and incubated with fluorescein isothiocyanate (FITC)-conjugated goat F(ab') antimouse-IgG (Sigma) for 30 min at 4° C. and washed four times as before. The cells were resuspended in staining buffer and fixed by adding a quarter volume of 2% paraformaldehyde. The analysis of surface HLA-A2.1 molecules stabilized by peptide binding was performed by flow cytometry using a FACScan (Becton Dickinson, San Jose, Calif.).

The results of the experiment are shown in FIG. 3. Using the method discussed above, a candidate tyrosinase housekeeping epitope identified by proteasomal digestion, (tyrosinase 207–216, FLPWHRLFLL SEQ ID NO: 60) was found to bind HLA-A2.1 to a similar extent as the known A2.1 binder FLPSDYFPSV (SEQ ID NO: 61)(positive control). HLA-B44 binding peptide AEMGKYSFY (SEQ ID NO: 62) used as a negative control. The fluoresence obtained from the negative control was similar to the signal obtained when no peptide was used in the assay. Positive and negative control peptides were chosen from Table 18.3.1 in *Current Protocols in Immunology* p. 18.3.2, John Wiley and Sons, New York, 1998.

What is claimed is:

1. A method of epitope discovery comprising the steps of:
choosing a neoplastic target cell;
identifying a proteasome activity of the target cell, wherein said proteasome is either a housekeeping proteasome or an immune proteasome; and
selecting an epitope from a population of peptide fragments of an antigen associated with the target cell, wherein the antigen is selected from the group consisting of MelanA (MART-1), gp100 (Pmel 17), tyrosinase, RP-1, TRP-2, MAGE-1, MAGE-3, BAGE, GAGE-1, GAGE-2, CEA, RAGE, NY-ESO, SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180crbB-3, c-met, nm-23H1, PSA, TAG-72-4, CAM 17.1, NuMa, K-ras, β-Catenin, CDK1, Mum-1, and p16, and wherein the fragments have a known or predicted affinity for a major histocompatibility complex class I receptor peptide binding cleft, wherein the epitope selected corresponds to a cleavage product associated with said proteasome activity of the target cell.

2. A method of epitope discovery comprising the steps of:
choosing a target cell that is infected by a virus;
identifying a proteasome activity of the target cell, wherein said proteasome is either a housekeeping proteasome or an immune proteasome; and
selecting an epitope from a population of peptide fragments of an antigen associated with the target cell, wherein the fragments have a known or predicted affinity for a major histocompatibility complex class I receptor peptide binding cleft, wherein the epitope selected corresponds to a cleavage product associated with said proteasome activity of the target cell.

3. The method of claim 2, wherein the virus is selected from the group consisting of: adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus BK, polyomavirus IC, hepatitis C virus, measles virus, rubella virus, human immunodeficiency virus (Hr), human T cell leukemia virus I, and human T cell leukemia virus II.

4. The method of claim 2, wherein the antigen is selected from the group consisting of adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus BK, polyomavirus JC, hepatitis C virus, measles virus, rubella virus, human immunodeficiency virus (HIV), human T cell leukemia virus I, and human T cell leukemia virus II.

5. A method of epitope discovery comprising the steps of:
choosing a target cell that is infected by an intracellular parasite, wherein the intracellular parasite is a bacterium, a protozoan, a fungus, or a prion;
identifying a proteasome activity of the target cell, wherein said proteasome is either a housekeeping proteasome or an immune proteasome; and
selecting an epitope from a population of peptide fragments of an antigen associated with the target cell, wherein the fragments have a known or predicted affinity for a major histocompatibility complex class I receptor peptide binding cleft, wherein the epitope selected corresponds to a cleavage product associated with said proteasome activity of the target cell.

6. The method of claim 5, wherein the intracellular parasite is selected from the group consisting of Chlamydia, Listeria, Salmonella, Legionella, Brucella, Coxiella, Rickettsia, Mycobacterium, Leishmania, Trypanasoma, Toxoplasma, and Plasmodium.

7. The method of claim 5, wherein the antigen is a parasite-associated antigen.

8. The method of claim 4, wherein the product is determined by in vitro analysis.

9. The method of claim 4, wherein the proteasome is a housekeeping proteasome.

10. The method of claim 4, wherein the proteasome is an immune proteasome.

11. A method of discovering an epitope comprising the steps of:
providing a sequence from a target cell, wherein the sequence encodes or comprises a protein expressed in the target cell, wherein the target cell is a neoplastic cell;
identifying a population of peptide fragments of the protein, wherein the protein is selected from the group consisting of MelanA (MART-I), gp100 (Pmel 17), tyrosinase, TRP-1, TRP-2, MAGE-1, MAGE-3, BAGE, GAGE-1, GAGE-2, CEA, RAGE, NY-ESO, SCP-1, Hom/Mel-40, PRAME, p53, H-Ras, HER-2/neu, BCR-ABL, E2A-PRL, H4-RET, IGH-IGK, MYL-RAR, Epstein Barr virus antigens EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CAM 17.1, NuMa, K-ras, β-Catenin, CDK4, Mum-1, and p16, wherein members of the population of peptide fragments have a known or predicted affinity for a major histocompatibility complex class I receptor peptide binding cleft; and
selecting either a housekeeping epitope or an immune epitope from the population of peptide fragments, based thin a proteasome that is active in the target cell, wherein the proteasome is a housekeeping proteasome or an in immune proteasome.

12. A method of discovering an epitope comprising the steps of:
providing a sequence from a target cell, wherein the sequence encodes or comprises a protein expressed in the target cell, wherein the target cell is infected by a virus;
identifying a population of peptide fragments of the protein, wherein members of the population of peptide fragments have a known or predicted affinity for a major histocompatibility complex class I receptor peptide binding cleft; and
selecting either a housekeeping epitope or an immune epitope from the population of peptide fragments, based upon a proteasome that is active in the target cell, wherein the proteasome is a housekeeping proteasome or an immune proteasome.

13. The method of claim 12, wherein the virus is selected from the group consisting of: adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus BK, polyomavirus JC, hepatitis C virus, measles virus, rubella virus, human immunodeficiency virus (HIV), human T cell leukemia virus I, and human T cell leukemia virus II.

14. The method of claim 12, wherein the antigen is selected from the group consisting of adenovirus, cytomegalovirus, Epstein-Bar virus, herpes simplex virus 1, herpes simplex virus 2, human herpesvirus 6, varicella-zoster virus, hepatitis B virus, hepatitis D virus, papilloma virus, parvovirus B19, polyomavirus BK polyomavirus JC, hepatitis C virus, measles virus, rubella virus, human immunodeficiency virus (HIV), human T cell leukemia virus I, and human T cell leukemia virus II.

15. A method of discovering an epitope comprising the steps of:
    providing a sequence from a target cell, wherein the sequence encodes or comprises a protein expressed in the target call, wherein the target cell is infected by an intracellular parasite, and wherein the intracellular parasite is a bacterium, a protozoan, a fungus, or a prion;
    identifying a population of peptide fragments of the protein, wherein members of the population of peptide fragments have a known or predicted affinity for a major histocompatibility complex class I receptor peptide binding cleft; and
    selecting either a housekeeping epitope or an immune epitope from the population of peptide fragments, based upon a proteasome that is active in the target cell, wherein the proteasome is a housekeeping proteasome or an immune proteasome.

16. The method of claim 15, wherein the intracellular parasite is selected from the group consisting of Chlamydia, Listeria, Salmonella, Legionella, Brucella, Coxiella, Rickettsia, Mycobacterium, Leishmania, Trypanasoma, Toxoplasma, and Plasmodium.

17. The method of claim 15 wherein the antigen is a parasite-associated antigen.

18. A method of discoing an epitope comprising the steps of:
    providing a sequence from a target cell, wherein the sequence encodes or comprises a protein expressed in the target cell, wherein the target cell is an intracellular parasite;
    identifying a population of peptide fragments of the protein, wherein members of the population of peptide fragments have a known or predicted affinity for a major histocompatibility complex class I receptor peptide binding cleft, wherein the affinity is determined by an algorithm; and
    selecting either a housekeeping epitope or an immune epitope from the population of peptide fragments, based upon a proteasome that is active in the target cell, wherein the proteasome is a housekeeping proteasome or an immune proteasome.

19. A method of epitope discovery comprising the steps of:
    providing a neoplastic cell and a sequence, wherein the sequence comprises or encodes an antigen associated with the neoplastic cell, wherein the antigen is selected from the group consisting of MelanA (MART-I), gp100 (Pmel 17), tyrosinase, TRP-1, TRP-2, MAGE-1, MAGE-3, BAGE, GAGE-1, GAGE-2, CEA, RAGE, NY-ESO, SCP-1, Hom/Mel-40, PRAME, p53, H-Ras, HER-2/neu, BCR-ABL, EZA-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CAM 17.1, NuMa, K-ras, β-Catenin, CDK4, Mum-1, and p16;
    identifying a population of peptide fragments of the antigen, wherein the population of peptide fragments is predicted to have an affinity for a major histocompatibility complex class I receptor peptide binding cleft; and
    selecting an epitope from the population of peptide fragments, wherein the epitope is determined by in vitro analysis to be a proteasome cleavage reaction product of a housekeeping proteasome or an immune proteasome active in the neoplastic cell.

* * * * *

SEQUENCE LISTING

<160> NUMBER OF SEQ ID NOS: 69

<210> SEQ ID NO 1
<211> LENGTH: 10
<212> TYPE: PRT
<213> ORGANISM: Homo sapien

<400> SEQUENCE: 1

Leu Gln Leu Ser Asn Gly Asn Arg Thr Leu
 1               5                   10

<210> SEQ ID NO 2
<211> LENGTH: 10
<212> TYPE: PRT
<213> ORGANISM: Homo sapien

<400> SEQUENCE: 2

Leu Gln Leu Ser Asn Asp Asn Arg Thr Leu
 1               5                   10

<210> SEQ ID NO 3
<211> LENGTH: 10
<212> TYPE: PRT
<213> ORGANISM: Homo sapien

<400> SEQUENCE: 3

Leu Gln Leu Ser Asn Gly Asn Arg Thr Leu
 1               5                   10

<210> SEQ ID NO 4
<211> LENGTH: 10
<212> TYPE: PRT
<213> ORGANISM: Homo sapien

<400> SEQUENCE: 4

Leu Leu Val His Asn Leu Pro Gln His Leu
 1               5                   10

<210> SEQ ID NO 5
<211> LENGTH: 10
<212> TYPE: PRT
<213> ORGANISM: Homo sapien

<400> SEQUENCE: 5

Leu Ser Asn Asp Asn Arg Thr Leu Thr Leu
 1               5                   10

<210> SEQ ID NO 6
<211> LENGTH: 10
<212> TYPE: PRT
<213> ORGANISM: Homo sapien

<400> SEQUENCE: 6

Leu Ser Asn Gly Asn Arg Thr Leu Thr Leu
 1               5                   10

<210> SEQ ID NO 7
<211> LENGTH: 10
<212> TYPE: PRT
<213> ORGANISM: Homo sapien

<400> SEQUENCE: 7

Leu Ser Asn Gly Asn Arg Thr Leu Thr Leu
 1               5                   10

<210> SEQ ID NO 8
<211> LENGTH: 10
<212> TYPE: PRT
<213> ORGANISM: Homo sapien

<400> SEQUENCE: 8

Cys Gln Ala His Asn Ser Asp Thr Gly Leu

```
                1               5                  10
```

<210> SEQ ID NO 9
<211> LENGTH: 10
<212> TYPE: PRT
<213> ORGANISM: Homo sapien

<400> SEQUENCE: 9

```
Ile Ile Tyr Pro Asn Ala Ser Leu Leu Ile
 1               5                  10
```

<210> SEQ ID NO 10
<211> LENGTH: 10
<212> TYPE: PRT
<213> ORGANISM: Homo sapien

<400> SEQUENCE: 10

```
Ser Ala Asn Arg Ser Asp Pro Val Thr Leu
 1               5                  10
```

<210> SEQ ID NO 11
<211> LENGTH: 10
<212> TYPE: PRT
<213> ORGANISM: Homo sapien

<400> SEQUENCE: 11

```
Ser Val Ser Ala Asn Arg Ser Asp Pro Val
 1               5                  10
```

<210> SEQ ID NO 12
<211> LENGTH: 10
<212> TYPE: PRT
<213> ORGANISM: Homo sapien

<400> SEQUENCE: 12

```
Ser Ile Ser Ser Asn Asn Ser Lys Pro Val
 1               5                  10
```

<210> SEQ ID NO 13
<211> LENGTH: 10
<212> TYPE: PRT
<213> ORGANISM: Homo sapien

<400> SEQUENCE: 13

```
Trp Trp Val Asn Asn Gln Ser Leu Pro Val
 1               5                  10
```

<210> SEQ ID NO 14
<211> LENGTH: 10
<212> TYPE: PRT
<213> ORGANISM: Homo sapien

<400> SEQUENCE: 14

```
Trp Trp Val Asn Asn Gln Ser Leu Pro Val
 1               5                  10
```

<210> SEQ ID NO 15
<211> LENGTH: 10
<212> TYPE: PRT
<213> ORGANISM: Homo sapien

<400> SEQUENCE: 15

```
Ser Ile Ser Ser Asn Asn Ser Lys Pro Val
 1               5                  10
```

-continued

```
<210> SEQ ID NO 16
<211> LENGTH: 10
<212> TYPE: PRT
<213> ORGANISM: Homo sapien

<400> SEQUENCE: 16

Ser Asp Leu Val Asn Glu Glu Ala Thr Gly
  1               5                  10

<210> SEQ ID NO 17
<211> LENGTH: 10
<212> TYPE: PRT
<213> ORGANISM: Homo sapien

<400> SEQUENCE: 17

Ile Thr Pro Asn Asn Asn Gly Thr Tyr Ala
  1               5                  10

<210> SEQ ID NO 18
<211> LENGTH: 10
<212> TYPE: PRT
<213> ORGANISM: Homo sapien

<400> SEQUENCE: 18

Ser Leu Pro Val Ser Pro Arg Leu Gln Leu
  1               5                  10

<210> SEQ ID NO 19
<211> LENGTH: 10
<212> TYPE: PRT
<213> ORGANISM: Homo sapien

<400> SEQUENCE: 19

Ser Leu Pro Val Ser Pro Arg Leu Gln Leu
  1               5                  10

<210> SEQ ID NO 20
<211> LENGTH: 10
<212> TYPE: PRT
<213> ORGANISM: Homo sapien

<400> SEQUENCE: 20

Phe Ile Thr Ser Asn Asn Ser Asn Pro Val
  1               5                  10

<210> SEQ ID NO 21
<211> LENGTH: 10
<212> TYPE: PRT
<213> ORGANISM: Homo sapien

<400> SEQUENCE: 21

Arg Ser Gly Glu Asn Leu Asn Leu Ser Cys
  1               5                  10

<210> SEQ ID NO 22
<211> LENGTH: 10
<212> TYPE: PRT
<213> ORGANISM: Homo sapien

<400> SEQUENCE: 22

Ser Leu Pro Val Ser Pro Arg Leu Gln Leu
  1               5                  10

<210> SEQ ID NO 23
```

```
<211> LENGTH: 10
<212> TYPE: PRT
<213> ORGANISM: Homo sapien

<400> SEQUENCE: 23

Val Tyr Pro Glu Leu Pro Lys Pro Ser Ile
 1               5                  10

<210> SEQ ID NO 24
<211> LENGTH: 10
<212> TYPE: PRT
<213> ORGANISM: Homo sapien

<400> SEQUENCE: 24

Ser Thr Pro Phe Asn Val Ala Glu Gly Lys
 1               5                  10

<210> SEQ ID NO 25
<211> LENGTH: 10
<212> TYPE: PRT
<213> ORGANISM: Homo sapien

<400> SEQUENCE: 25

Asn Pro Pro Thr Thr Ala Lys Leu Thr Ile
 1               5                  10

<210> SEQ ID NO 26
<211> LENGTH: 10
<212> TYPE: PRT
<213> ORGANISM: Homo sapien

<400> SEQUENCE: 26

Cys Phe Val Ser Asn Leu Ala Thr Gly Arg
 1               5                  10

<210> SEQ ID NO 27
<211> LENGTH: 10
<212> TYPE: PRT
<213> ORGANISM: Homo sapien

<400> SEQUENCE: 27

Gly Ala Asn Leu Asn Leu Ser Cys His Ser
 1               5                  10

<210> SEQ ID NO 28
<211> LENGTH: 10
<212> TYPE: PRT
<213> ORGANISM: Homo sapien

<400> SEQUENCE: 28

Leu Ser Gly Ala Asn Leu Asn Leu Ser Cys
 1               5                  10

<210> SEQ ID NO 29
<211> LENGTH: 10
<212> TYPE: PRT
<213> ORGANISM: Homo sapien

<400> SEQUENCE: 29

Ser Tyr Leu Ser Gly Ala Asn Leu Asn Leu
 1               5                  10

<210> SEQ ID NO 30
<211> LENGTH: 10
<212> TYPE: PRT
```

<213> ORGANISM: Homo sapien

<400> SEQUENCE: 30

Cys Gly Ile Gln Asn Ser Val Ser Ala Asn
 1               5                  10

<210> SEQ ID NO 31
<211> LENGTH: 10
<212> TYPE: PRT
<213> ORGANISM: Homo sapien

<400> SEQUENCE: 31

Val Ser Ala Glu Leu Pro Lys Pro Ser Ile
 1               5                  10

<210> SEQ ID NO 32
<211> LENGTH: 10
<212> TYPE: PRT
<213> ORGANISM: Homo sapien

<400> SEQUENCE: 32

Ser Asn Ile Thr Glu Lys Asn Ser Gly Leu
 1               5                  10

<210> SEQ ID NO 33
<211> LENGTH: 10
<212> TYPE: PRT
<213> ORGANISM: Homo sapien

<400> SEQUENCE: 33

Gly Asn Ile Gln Gln His Thr Gln Glu Leu
 1               5                  10

<210> SEQ ID NO 34
<211> LENGTH: 10
<212> TYPE: PRT
<213> ORGANISM: Homo sapien

<400> SEQUENCE: 34

Ser Asn Pro Pro Ala Gln Tyr Ser Trp Leu
 1               5                  10

<210> SEQ ID NO 35
<211> LENGTH: 10
<212> TYPE: PRT
<213> ORGANISM: Homo sapien

<400> SEQUENCE: 35

Cys Gly Ile Gln Asn Glu Leu Ser Val Asp
 1               5                  10

<210> SEQ ID NO 36
<211> LENGTH: 10
<212> TYPE: PRT
<213> ORGANISM: Homo sapien

<400> SEQUENCE: 36

Ile Ser Pro Leu Asn Thr Ser Tyr Arg Ser
 1               5                  10

<210> SEQ ID NO 37
<211> LENGTH: 10
<212> TYPE: PRT
<213> ORGANISM: Homo sapien

```
<400> SEQUENCE: 37

Pro Gly Pro Ala Tyr Ser Gly Arg Glu Ile
 1               5                  10

<210> SEQ ID NO 38
<211> LENGTH: 10
<212> TYPE: PRT
<213> ORGANISM: Homo sapien

<400> SEQUENCE: 38

Phe Asn Val Ala Glu Gly Lys Glu Val Leu
 1               5                  10

<210> SEQ ID NO 39
<211> LENGTH: 10
<212> TYPE: PRT
<213> ORGANISM: Homo sapien

<400> SEQUENCE: 39

Ile Gly Val Leu Val Gly Val Ala Leu Ile
 1               5                  10

<210> SEQ ID NO 40
<211> LENGTH: 10
<212> TYPE: PRT
<213> ORGANISM: Homo sapien

<400> SEQUENCE: 40

Ser Ala Gly Ala Thr Val Gly Ile Met Ile
 1               5                  10

<210> SEQ ID NO 41
<211> LENGTH: 10
<212> TYPE: PRT
<213> ORGANISM: Homo sapien

<400> SEQUENCE: 41

Ser Lys Pro Val Glu Asp Lys Asp Ala Val
 1               5                  10

<210> SEQ ID NO 42
<211> LENGTH: 10
<212> TYPE: PRT
<213> ORGANISM: Homo sapien

<400> SEQUENCE: 42

Ser Ala Ser Gly His Ser Arg Thr Thr Val
 1               5                  10

<210> SEQ ID NO 43
<211> LENGTH: 10
<212> TYPE: PRT
<213> ORGANISM: Homo sapien

<400> SEQUENCE: 43

Arg Pro Gly Val Asn Leu Ser Leu Ser Cys
 1               5                  10

<210> SEQ ID NO 44
<211> LENGTH: 10
<212> TYPE: PRT
<213> ORGANISM: Homo sapien

<400> SEQUENCE: 44
```

```
Leu Ser Val Asp His Ser Asp Pro Val Ile
1               5                   10
```

<210> SEQ ID NO 45
<211> LENGTH: 10
<212> TYPE: PRT
<213> ORGANISM: Homo sapien

<400> SEQUENCE: 45

```
Ser Asn Asp Asn Arg Thr Leu Thr Leu Leu
1               5                   10
```

<210> SEQ ID NO 46
<211> LENGTH: 10
<212> TYPE: PRT
<213> ORGANISM: Homo sapien

<400> SEQUENCE: 46

```
Ser Asn Pro Val Glu Asp Glu Asp Ala Val
1               5                   10
```

<210> SEQ ID NO 47
<211> LENGTH: 10
<212> TYPE: PRT
<213> ORGANISM: Homo sapien

<400> SEQUENCE: 47

```
Ser Asn Asn Ser Asn Pro Val Glu Asp Glu
1               5                   10
```

<210> SEQ ID NO 48
<211> LENGTH: 10
<212> TYPE: PRT
<213> ORGANISM: Homo sapien

<400> SEQUENCE: 48

```
Gly Leu Asn Arg Thr Thr Val Thr Thr Ile
1               5                   10
```

<210> SEQ ID NO 49
<211> LENGTH: 10
<212> TYPE: PRT
<213> ORGANISM: Homo sapien

<400> SEQUENCE: 49

```
Ile Thr Val Asn Asn Ser Gly Ser Tyr Thr
1               5                   10
```

<210> SEQ ID NO 50
<211> LENGTH: 10
<212> TYPE: PRT
<213> ORGANISM: Homo sapien

<400> SEQUENCE: 50

```
Ser Thr Gln Glu Leu Phe Ile Pro Asn Ile
1               5                   10
```

<210> SEQ ID NO 51
<211> LENGTH: 10
<212> TYPE: PRT
<213> ORGANISM: Homo sapien

<400> SEQUENCE: 51

```
Phe Gln Gln Ser Thr Gln Glu Leu Phe Ile
1               5                   10
```

<210> SEQ ID NO 52
<211> LENGTH: 10
<212> TYPE: PRT
<213> ORGANISM: Homo sapien

<400> SEQUENCE: 52

Ser Ala Arg Arg Ser Asp Ser Val Ile Leu
1               5                   10

<210> SEQ ID NO 53
<211> LENGTH: 10
<212> TYPE: PRT
<213> ORGANISM: Homo sapien

<400> SEQUENCE: 53

Val Ser Ala Arg Arg Ser Asp Ser Val Ile
1               5                   10

<210> SEQ ID NO 54
<211> LENGTH: 10
<212> TYPE: PRT
<213> ORGANISM: Homo sapien

<400> SEQUENCE: 54

Ser Lys Pro Val Glu Asp Lys Asp Ala Val
1               5                   10

<210> SEQ ID NO 55
<211> LENGTH: 10
<212> TYPE: PRT
<213> ORGANISM: Homo sapien

<400> SEQUENCE: 55

Thr Gly Gln Phe Arg Val Tyr Pro Glu Leu
1               5                   10

<210> SEQ ID NO 56
<211> LENGTH: 10
<212> TYPE: PRT
<213> ORGANISM: Homo sapien

<400> SEQUENCE: 56

Lys Glu Val Leu Leu Val His Asn Leu
1               5                   10

<210> SEQ ID NO 57
<211> LENGTH: 10
<212> TYPE: PRT
<213> ORGANISM: Homo sapien

<400> SEQUENCE: 57

Ala Lys Leu Thr Ile Glu Ser Thr Pro Phe
1               5                   10

<210> SEQ ID NO 58
<211> LENGTH: 9
<212> TYPE: PRT
<213> ORGANISM: Homo sapien

<400> SEQUENCE: 58

Ala Leu Met Asp Lys Ser Leu His Val
1               5

```
<210> SEQ ID NO 59
<211> LENGTH: 10
<212> TYPE: PRT
<213> ORGANISM: Homo sapien

<400> SEQUENCE: 59

Ser Leu His Val Gly Thr Gln Cys Ala Leu
1               5                   10

<210> SEQ ID NO 60
<211> LENGTH: 10
<212> TYPE: PRT
<213> ORGANISM: Homo sapien

<400> SEQUENCE: 60

Phe Leu Pro Trp His Arg Leu Phe Leu Leu
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic HLA Binding Peptide

<400> SEQUENCE: 61

Phe Leu Pro Ser Asp Tyr Phe Pro Ser Val
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Synthetic HLA Binding Peptide

<400> SEQUENCE: 62

Ala Glu Met Gly Lys Tyr Ser Phe Tyr
1               5

<210> SEQ ID NO 63
<211> LENGTH: 16
<212> TYPE: PRT
<213> ORGANISM: Artificial Sequence
<220> FEATURE:
<223> OTHER INFORMATION: Immune Proteasome Assay Positive Control
      Peptide

<400> SEQUENCE: 63

Met Leu Leu Ala Val Leu Tyr Cys Leu Leu Trp Ser Phe Gln Thr Ser
1               5                   10                  15

<210> SEQ ID NO 64
<211> LENGTH: 22
<212> TYPE: PRT
<213> ORGANISM: Artificial Sequence
<220> FEATURE:
<223> OTHER INFORMATION: Immune Proteasome Assay Positive Control
      Peptide

<400> SEQUENCE: 64

His Ser Tyr Thr Thr Ala Glu Glu Ala Ala Gly Ile Thr Ile Leu Thr
1               5                   10                  15

Val Ile Leu Gly Val Leu
            20
```

-continued

```
<210> SEQ ID NO 65
<211> LENGTH: 24
<212> TYPE: PRT
<213> ORGANISM: Artificial Sequence
<220> FEATURE:
<223> OTHER INFORMATION: Immune Proteasome Assay Positive Control
      Peptide

<400> SEQUENCE: 65

Glu Ala Ala Ser Ser Ser Ser Thr Leu Val Glu Val Thr Leu Gly Glu
1               5                   10                  15

Val Pro Ala Ala Glu Ser Pro Asp
            20

<210> SEQ ID NO 66
<211> LENGTH: 24
<212> TYPE: PRT
<213> ORGANISM: Artificial Sequence
<220> FEATURE:
<223> OTHER INFORMATION: Immune Proteasome Assay Positive Control
      Peptide

<400> SEQUENCE: 66

Glu Phe Leu Trp Gly Pro Arg Ala Leu Val Glu Thr Ser Tyr Val Lys
1               5                   10                  15

Val Leu His His Met Val Lys Ile
            20

<210> SEQ ID NO 67
<211> LENGTH: 19
<212> TYPE: PRT
<213> ORGANISM: Artificial Sequence
<220> FEATURE:
<223> OTHER INFORMATION: Immune Proteasome Assay Positive Control
      Peptide

<400> SEQUENCE: 67

Ala Pro Glu Glu Lys Ile Trp Glu Glu Leu Ser Val Leu Glu Val Phe
1               5                   10                  15

Glu Gly Arg

<210> SEQ ID NO 68
<211> LENGTH: 16
<212> TYPE: PRT
<213> ORGANISM: Artificial Sequence
<220> FEATURE:
<223> OTHER INFORMATION: Immune Proteasome Assay Positive Control
      Peptide

<400> SEQUENCE: 68

Glu Leu Met Glu Val Asp Pro Ile Gly His Leu Tyr Ile Phe Ala Thr
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Housekeeping Proteasome Assay Positive
      ControlPeptide

<400> SEQUENCE: 69

Phe Leu Trp Gly Pro Arg Ala Leu Val Glu Thr Ser Tyr Val Lys
1               5                   10                  15
```